United States Patent [19]

Friedmann et al.

[11] Patent Number: 5,643,875

[45] Date of Patent: Jul. 1, 1997

[54] HUMAN THERAPEUTIC USES OF BACTERICIDAL/PERMEABILITY INCREASING (BPI) PROTEIN PRODUCTS

[76] Inventors: Nadav Friedmann, 91 Bacon Ct., Lafayette, Calif. 94549; Patrick J. Scannon, 176 Edgewood Ave., San Francisco, Calif. 94117; Sander J. H. van Deventer; Marijke A. M. von der Mohlen, both of Meibergdreff 9, 1105 AZ, Amsterdam, Netherlands; Nancy Wedel, 5800 Ayala Ave., Oakland, Calif. 94609

[21] Appl. No.: 291,112

[22] Filed: Aug. 16, 1994

Related U.S. Application Data

[63] Continuation-in-part of Ser. No. 188,221, Jan. 24, 1994, abandoned.

[51] Int. Cl.$^6$ .......................... A61K 38/00; A61K 45/05
[52] U.S. Cl. .................. 514/12; 514/21; 514/921; 530/324; 530/325; 530/351; 530/820; 424/85.1; 424/85.2; 424/529; 424/534
[58] Field of Search .................. 514/12, 21, 921; 530/324, 325, 820, 351; 424/85.1, 85.2, 529, 534

[56] References Cited

U.S. PATENT DOCUMENTS

| 5,089,274 | 2/1992 | Maraa et al. | 424/534 |
| 5,171,739 | 12/1992 | Scott | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |

FOREIGN PATENT DOCUMENTS

| WO90/09183 | 8/1990 | WIPO . |
| WO92/03535 | 3/1992 | WIPO . |
| WO92/35353 | 3/1992 | WIPO . |
| WO92/09621 | 6/1992 | WIPO . |

OTHER PUBLICATIONS

Ammons et al., "Protective Effects of an N-Terminal Fragment of Bactericidal/Permeability–Increasing Protein in Rodent Models of Gram–Negative Sepsis: Role of Bactericidal Properties," *J. Infect. Dis.*, 170(6):1473–82 (Dec. 1994).

Ammons et al., "Protective Effects of an N-Terminal Fragment of Bactericidal/Permeability–Increasing Protein in Endotoxemia and Gram–Negative Sepsis," *Novel Therapeutics Strategies in the Treatment of Sepsis*, pp. 55–70 (1996).

Ammons et al., "An N–Terminal Fragment of Bactericidal/Permeability–Increasing Protein Protects against Hemodynamic and Metabolic Derangements in Rat Gram–Negative Sepsis," *J. Endotoxin Res.*, 3(1):57–66 (1996).

Boermeester et al., "Liver Failure Induces a Systemic Inflammatory Response," *Amer. J. Pathology*, 147(5):1428–1440 (Nov. 1995).

Evans et al., "Protective Effects of a Recombinant Amino–Terminal of Human Bactericidal/Permeability–Increasing Protein in an Animal Model of Gram–Negative Sepsis," *J. Infect. Dis.*, 171:153–60 (Jan. 1995).

Kohn et al., "Role of Endotoxin in Acute Inflammation Induced by Gram–Negative Bacteria:Specific Inhibition of Lipopolysaccharide–Mediated Responses with an Amino–Terminal Fragment of Bactericidal/Permeability–Increasing Protein," *Infect. Immun.*, 63(1):333–339 (Jan. 1995).

Koyama et al., "rBPI$_{23}$ Attenuates Endotoxin–Induced Cardiovascular Depression in Awake Rabbits," *SHOCK*, 4(1):74–78 (Jul. 1995).

Kung et al., "Efficacy of a recombinant terminal fragment of bactericidal/permeability increasing protein in rodents challenged with LPS or *E. coli* bacteria," *In Bacterial Endotoxins: Basic Science to Anti–Sepsis Strategies*, Wiley–Liss, New York, pp. 255–263 (1994).

Lechner et al., "The Recombinant 23–kDa N–Terminal Fragment of Bactericidal/Permeability–Increasing Protein (rBPI$_{23}$) Decreases *Escherichia Coli*–Induced Mortality and Organ Injury During Immunosuppression–Related Neutropenia," *SHOCK*, 4(4):298–306 (Nov. 1995).

Litchman et al., "Reactivation of Arthritis Induced by Small Bowel Bacterial Overgrowth in Rats: Role of Cytokines, Bacteria, and Bacterial Polymers," *Infect. Immun.*, 63(6):2295–2301 (Jun. 1995).

Lin et al., "Protective Effects of a Recombinant N–Terminal Fragment of Bactericidal/Permeability Increasing Protein on Endotoxic Shock in Conscious Rabbits," *SHOCK*, 2(5):324–331 (Nov. 1994).

Lin et al., "Protective Effect Of A Recombinant Fragment Of Bactericidal/Permeability Increasing Protein Against Carbohydrate Dyshomeostasis And Tumor Necrosis Factor–αElevation In Rate Endotoxemia," *Biochem. Pharmacol.* 47(9):1553–1559 (Apr. 1994).

Lin et al., "Synergistic Effect of a Recombinant N–Terminal Fragment of Bactericidal/Permeability–Increasing Protein and Cefamandole in Treatment of Rabbit Gram–Negative Sepsis," *Antimicrobial Agents and Chemotherapy*, 40(1):65–69 (Jan. 1996).

(List continued on next page.)

*Primary Examiner*—Elizabeth C. Weimar
*Assistant Examiner*—Abdel A. Mohamed

[57] ABSTRACT

Disclosed are methods for treatment of humans exposed to bacterial endotoxin in circulation by administration of bactericidal/permeability-increasing (BPI) protein products. Serologically and hematologically verifiable alleviation of endotoxin mediated increases in circulating cytokines, fibrinolysis and coagulation factors and changes in lymphocyte counts are observed upon such treatment. Also observed is alleviation of endotoxin mediated decreases in systemic vascular resistance index (SVRI) and concomitant increases in cardiac index (CI).

12 Claims, 19 Drawing Sheets

OTHER PUBLICATIONS

Schlag et al., "Protective Effect of Bactericidal/Permeability–Increasing Protein (rBPI$_{21}$) on Sepsis Induced Organ Failure in Nonhuman Primates," SHOCK Conference, Ashville, N.C. Jun. 11–14, 1995.

VanderMeer et al., "Bactericidal/Permeability–Increasing Protein Ameliorates Acute Lung Injury in Porcine Endotoxemia," J. Infect. Dis., 172(1):2006–14 (May 1994).

Yao et al., "Pathogenesis of Hemorrhage–Induced Bacteria/Endotoxin Translocation in Rats," Annals Surg., 221(4):398–405 (Apr. 1995).

Barron, "Pathophysiology of Septic Shock and Implications for Therapy", Clinical Pharmacy, 12(11):829–845 (Nov. 1993).

Meszaros et al., "A Recombinant Amino Terminal Fragment of Bactericidal/Permeability–Increasing Protein Inhibits the Induction of Leukocyte Responses by LPS", J. Leukocyte Biol., 54(6):558–563 (Dec. 1993).

van Leeuwan et al., "Hepatic failure and coma after liver resection is reversed by manipulation of gut contents: The role of endotoxin," Surgery, 110(2):169–175 (Aug. 1991).

Boermeester et al., Abstract, "Bactericidal/permeability–increasing protein (BPI) prevents hemodynamic and metabolic derangements following partial hepatectomy" presented at Dutch Society of Gastroenterology Meeting, Oct. 7, 1993.

Ammons et al., "Recombinant Amino Terminal Fragment of Bactericidal/Permeability Increasing Protein Prevents Hemodynamic Responses to Endotoxin", Circulatory Shock, 41;176–184 (1993).

Baggiolini et al., "Neutrophil–activating Peptide–1/Interleukin 8, a Novel Cytokine That Activates Neutrophils", J. Clin. Invest., 84:1045–1049 (Oct., 1989).

Berry, "Cellular Biology of Endotoxin, Introduction" Handbook of Endotoxin, vol. 3, pp. xvii–xxi, (1985).

Bloom et al., "Serum Neopterin Levels Following Intravenous Endotoxin Administration to Normal Humans", Immunobiol., 181:317–323 (1990).

Bone et al., "Definitions for sepsis and organ failure", Critical Care Medicine, 20(6):724–726 (1992).

Bradley et al., "Hemodynamic Alterations in Normotensive and Hypertensive Subjects During the Pyrogenic Reaction", J. Clin. Invest., 24:749–758 (1945).

Brigham et al., "Endotoxin and Lung Injury", Rev. Respir. Dis., 133:913–927 (1986).

Boujoukos et al., "Compartmentalization of the acute cytokine response in humans after intravenous endotoxin administration", J. Appl. Physiol., 74:3027–3033 (1993).

Boujoukos et al., "Detection of Interleukin–8 in Bronchoalveolar Lavage Without Alveolar Neutrophil Influx, Before and After Intravenous Endotoxin in Normal Humans", Am. Rev. Resp. Dis., 145(4):A441 (Apr. 1992).

Calandra et al., "Prognostic Values of Tumor Necrosis Factor/Cachetin, Interleukin–1, Interferon–α–and Interferon–μ in the Serum of Patients with Septic Shock", J. Infectious Diseases, 161:928–987 (1990).

Calandra et al., "High Circulating Levels of Interleukin–6 in Patients with Septic Shock: Evolution During Sepsis, Prognostic Value, and Interplay with Other Cytokines", Am. J. Medicine, 91:23–29 (Jul. 1991).

Canon et al., "Circulating Interleukin 1 and Tumor Necrosis Factor in Septic Shock and Experimental Endotoxin Fever", J. Infection Diseases, 161:79–84 (1990).

Cochrane, "The Enhancement of Inflammatory Injury", Am. Rev. Respir. Dis., 136:1–2 (1980).

Colman, "Surface–mediated Defense Reactions, The Plasma Contact Activation System", J. Clin. Invest., 73:1249–1253 (May 1984).

Danner et al., "Endotoxemia in Human Septic Shock", Chest, 99:169–175 (Jan. 1991).

DeLa Cadena et al., "Activation of the Kallikrein–Xn System After Endotoxin Administration to Normal Human Volunteers", Blood, 81(12):3313–3317 (Jun. 15, 1993).

Dinatello, "The Proinflamatory Cytokines Interleukin–1 and Tumor Necrosis Factor and Treatment of the Septic Shock Syndrome", J. Infection Diseases, 163:1177–1184 (1991).

Elin et al., "Effect of Induced Fever on Serum Iron and Ferritin Concentrations in Man", Blood, 49(1):147–153 (Jan. 1977).

Elsbach et al., "Separation and Purification of a Potent Bactericidal/Permeability Increasing Protein and a Closely Associated Phospholipase A2 from Rabbit Polymorphonuclear Leukocytes", J. Biol. Chem., 254:11000 (1979).

Elsbach et al., "Oxygen–Independent Antimicrobial Systems of Phagocytes" Inflammation: Basic Principles and Clinical Correlates, Chapter 30, pp. 603–636, 2nd. Ed., (1990).

Fong et al., "Endotoxemia Elicits Increased Cuiculating B2–IFN/IL–6 in Man", J. Immunology, 142(7):2321–2324 (Apr. 1, 1989).

Fong et al., "The Acute Splanchnic and Peripheral Tissue Metabolic Reponse to Endotoxin in Humans", J. Clin. Invest., 85:1896–1904 (1990).

Fong et al., "Total Parental Nutrition and Bowel Rest Modify the Metabolic Response to Endotoxin in Humans", Ann. Surg., 210:449–457 (1989).

Gazzano–Santoro et al., "High–Affinity Binding of the Bactericidal/Permeability–Increasing Protein and a Recombinant Amino–Terminal Fragment to the Lipid A Region of Lipopolysaccharide", Infect. Immun. 60(11):4754–4761 (Nov. 1992).

Granowitz et al., "Production of interleukin–1–receptor antagonist during experimental endotoxaemia", Lancet, 338:1423–24 (1991).

Granowitz et al., "Hematologic and Immunomoedulatory Effects of an Interleukin–1 Receptor Antagonist Contusion During Low–Dose Endoxemia in Healthy Humans", Blood, 82(10):2985–2990 (1993).

Gray et al., "Cloning of the cDNA of a Human Neutrophil Bactericidal Protein", J. Biol. Chem., 264(16):9505–9509 (Jun. 5, 1989).

Hack et al., "A Modified Competitive Inhibition Radioimmunoassay for the Detection of C3a", J. Immunol. Meth., 108:77–84 (1988).

Hesse et al., "Cytokine Appearance in Human Endotoxemia and Primate Bacteremia", Surg. Gyn. & Obstet., 166:147–153 (Feb. 1988).

In't Veld., "Effects of the Bactericidal/Permeability–Increasing Protein of Polymorphonuclear Leukocytes on Isolated Bacterial Cytoplasmic Membrane Vesicles", Infect. Immun., 56(5):1203–1208 (1988).

Kelly et al., "Role of the bactericidal permeability–increasing protein in the treatment if gram–negative pneumonia", Surgery, 114(2):140–146 (Aug. 1993).

Kindt et al., "Initial recruitment of neutrophils to alveolar structures in acute lung injury", J. Appl. Physiol., 70:1575–1585 (1991).

Kohn et al., "Protective Effect of a Recombinant Amino–Terminal Fragment of Bactericidal Permeability–Increasing Protein in Experimental Endotoxemia", *J. Infect. Diseases*, 166:1307–1310 (Nov. 1993).

Kung et al., International Conference on Endotoxemia IV, Amsterdam, The Netherlands, p. 23, Abstr. P3 (Aug. 17–29, 1993).

Leach et al., "Prevention of Lethal Endotoxemia by $BP_{23}$", *J. Cell. Chem.*, (Keystone Symposia, Suppl. 16(C):172:Abstr. CB 412, (Feb. 21–Mar. 7, 1992).

Levy et al., "Antibacterial 15–kDa Protein Isoforms (p15s) Are Members of a Novel Family of Leukocyte Proteins", *J. Biol. Chem.*, 268:6058–6063 (1993).

MacIntyre et al., "E5 Antibody Improves Outcome from Multi–Organ Failure in Survivors of Gram–Negative Sepsis", *Critical Care Medicine*, S14 (Apr. 1991).

Mannion et al., "Separation of Sublethal and Lethal Effects of Polymorphonuclear Leukocytes on *Escheria coli*", *J. Clin. Invest.*, 86:631–641 (Aug. 1990).

Marra et al., "The Role of Bactericidal/Permeability–increasing Protein as a Natural Inhibitor of Bacterial Endotoxin", *J. Immunol.*, 148(2):532–537 (Jan. 15, 1992).

Marra et al., "Bactericidal/Permeability–Increasing Protein Has Endotoxin–Neutralizing Activity", *J. Immunol*, 144(2):662–666 (Jan. 15, 1990).

Martich et al., "Intravenous Endotoxin Administration to Normal Humans Primes Neutrophils for an Enhanced Respiratory Burst", *Critical Care Medicine*, 5100 (Apr. 1992).

Martich et al., "Detection of Interleukin 8 and Tumor Necrosis Factor in Normal Humans after Intravenous Endotoxin: The Effect of Antiinflammatory Agents", *J. Exp. Medicine*, 173:1021–1024 (Apr. 1991).

Martich et al., "Effects of ibuprofen and pentoxifylline on the cardiovascular response of normal humans to endotoxin", *J. Appl. Physiol.*, 73:925–931m (1992).

Martich et al., "Response of Man to Endotoxin", *Immunobiol.*, 187:403–416 (Apr., 1993).

Michie et al., "Detection of Circulating Tumor Necrosis Factor After Endotoxin Administration", *N. Eng. J. Medicine*, 318(23):1481–1486 (Jun. 9, 1988).

Moore et al., "A Single Dose of Endotoxin Activates Neutrophils without Activating Complement", *Surgery*, 102:200–205 (Feb. 12–14, 1987).

Moser, et al., "Cardiopulmonary Consequences of Pyrogen–Induced Hyperpyrexia in Man", *J. Clin. Invest.*, 42(5):626–634 (1963).

Natanson et al., "Role of Endotoexmia in Cardiovascular Dysfunction and Mortally", *J. Clin. Invest.*, 83:243–251 (Jan. 1989).

Nuijens et al., "Plasma Elastase a1—antitrypsin and lactoferrin in sepsis: Evidence of neutrophils as mediators in fatal sepsis", *J. Lab. Clin. Med.*, 119:159–168 (1992).

Ooi et al., "A 25–kDa $NH_2$–terminal Fragment Carries All the Antibacterial Activities of the Human Neutrophil 60–kDa Bactericidal/Permeability–increasing Protein", *J. Biol. Chem.*, 262(31):14891–14894 (1987).

Ooi et al., "Endotoxin neutralizing Properties of the 25 kD N–Terminal Fragment of the 55–60 kD Bactericidal/Permeability–increasing Protein of Human Neutrophils", *J. Exp. Med.*, 174:649–655 (Sep. 1991).

Parrillo et al., "Septic Shock in Humans", *Annals of Int. Med.* 113(3):227–242 (1990).

Pruzanski et al., "Hyperphospholipasemia $A_2$ in Human Volunteers Challenged with Intravenous Endotoxin", *Inflammation* 16(5):561–570 (1992).

Revhaug et al., "Inhibition of Cyclo–oxygenase Attenuates the Metabolic Response to Endotoxin in Humans", *Arch. Surg.* 123:162–170 (Feb. 1988).

Smith et al., "Endotoxin Administration to Normal Humans Causes Increased Alveolar Permeability and Priming of Alveolar Macrophages to Produce Enhanced Superoxide and 11–1 Production", *Clin. Re:.* 36:374A (Apr. 1988).

Spinas et al, "Induction of plasma inhibitors of interleukin 1 and TNF–α activity by endotoxin administration to normal humans", *Am. J. Physiol.*, 259:R933–R997 (1990).

Spinas et al., "Pretreatment with Ibuprofen Augments Circulating Tumor Necrosis Factor–u, Interleukin–6, and Elastase during Acute Endotoxinemia", *J. Infectious Dis.*, 163:89–85 (1991).

Sturk et al., "Optimalization of a Chromogenic Assay for Endotoxin in Blood", *Bacterial Endotoxins*: Structure, Biomedical Significance, and Detection with the Limulus Amebocyte Lysate Test, pp. 117–136 (1985).

Suffredini et al., "Promotion and Subsequent Inhibition of Plasminogen Activation after Administration of Intravenous Endotoxin to Normal Subjects", *N. Eng. J. Medicine*, 320(18):1165–1172 (May 4, 1989).

Suffredini et al., "The Cardiovascular Response of Normal Humans to the Administration of Endotoxin", *N. Eng. J. Medicine*, 321:280–287 (Aug., 3 1989).

Suffredini et al., "Pulmonary and Oxygen Transport Effects of Intravenously Administered Endotoxin in Normal Humans", *Am. Rev. Respir. Dis.*, 145:1398–1403 (1992).

van Deventer et al., "Experimental Endotoxemia in Humans: Analysis of Cytokine Release and Coagulation, Fibrinolytic, and Complement Pathways", *Blood*, 76(12):2520–2526 (Dec. 15, 1990).

Van Zee et al., "Tumor necrosis factor soluble receptors circulate during experimental and clinical inflammation and can protect against excessive tumor necrosis facto, α in vitro and in vivo", *Proc. Natl. Acad. Sci. USA.*, 89:4845–4849 (Jun. 1992).

Van Zee et al., "Tumor Necrosis Factor (TNF) Soluble Receptors Protect Against Excessive TNFα During Infection and Injury", *FASEB* 6:A1715 (1992).

von der Mohlen et al., "Effect of $rBPI_{23}$ on Endotoxin–inducted Cytokine Release and Leukocyte Changes in Human Volunteers" Abstract (Apr. 29–May 2, 1994).

Wage et al., "The Complex Pattern of Cytokines in Serum from Patients with Meningococcal Septic Shock", *J. Exp. Med.* 169:333–338 (Jan. 1989).

Weiss et al., "Resistance of Gram–negative Bacteria to Purified Leukocyte Proteins", *J. Clin. Invest.*, 65:619–628 (Mar. 1980).

Weiss et al., "The Role of Lipopolysaccharide in the Action of the Bactericidal/Permeability Neutrophil Protein on the Bacterial Envelope", *J. Immunol.*, 132:3109–3115 (1984).

Weiss et al., "Cellular and Subcellular Localization of the Bactericidal/Permeability–Increasing Protein of Neutrophils", *Blood*, 69:652 (Feb. 1987).

Weiss et al., "Tissue Destruction by Neutrophils", *N. Eng. J. Medicine*, 320(6):365–376 (Feb. 9, 1989).

Wolff, "Biological Effects of Bacterial Endotoxins in Man", *J. Infectious Diseases* 128:5259–5264 (Jul. 1973).

Zabel et al., "Oxpentifylline in Endotoxaemia", *Lancet*, 2:1474–1477 (Dec. 23/30, 1989).

HUMAN THERAPEUTIC USES OF BACTERICIDAL/PERMEABILITY INCREASING (BPI) PROTEIN PRODUCTS

CROSS-REFERENCE TO RELATED APPLICATION

This is a continuation-in-part of U.S. patent application Ser. No. 08/188,221, filed Jan. 24, 1994, now abandoned.

BACKGROUND OF THE INVENTION

The present invention relates generally to therapeutic methods and more particularly to methods for treatment of humans exposed to bacterial endotoxin in blood circulation as a result of, e.g., Gram negative bacterial infection, accidental injection of endotoxin-contaminated fluids, translocation of endotoxin from the gut, release of endotoxin into circulation as a result of antibiotic mediated bacterial cytolysis and the like.

Gram negative bacterial endotoxin plays a central role in the pathogenesis of gram negative sepsis and septic shock, conditions which remain leading causes of morbidity and death in critically ill patients. Endotoxin interacts with inflammatory cells, releasing endogenous mediators such as cytokines, hydrolases, peptides, prostaglandins and other compounds that contribute to the pathophysiology of septic shock. While principal causes of entry of endotoxin into circulation are Gram negative bacteremia and translocation of bacteria and bacterial products from the gut, endotoxin also may enter circulation as the result of accidental injection of contaminated fluids or through release of endotoxin from bacteria lysed as a consequence of antibiotic therapy. In the recent past, therapeutic methods proposed for treatment of sepsis and septic shock have had as their focus attempts to bind endotoxin in circulation and inhibit direct and indirect release into circulation of proinflammatory substances mediated by the presence of endotoxin. Anti-endotoxin antibodies, for example, have shown promise in inhibition of endotoxin effects in humans.

A difficulty consistently encountered in developing therapeutic methods and materials for treatment of endotoxemia in humans has been the general unreliability of in vitro and even non-human in vivo test results as an indicator of human therapeutic potential. Because the effects of endotoxin in circulation are complex and involve direct and indirect responses by many cell types in the body, test results in attempts to intervene in endotoxin's effects on a particular cell type in vitro present an incomplete basis for assessment of in vivo effects. Animal studies are complicated by differences in the effect of bacterial endotoxin on different animal species and in different models with the same species. While humans are exquisitely sensitive to endotoxin, the responses of other animals vary significantly. For example, mice and rats are far more resistant to endotoxin on a weight basis than are rabbits and dogs; a life-threatening dose in rabbits would produce minimal effects in mice. Moreover, the types of effects noted are quite variable. Dogs display intestinal hemorrhages following sublethal but shock-producing doses of endotoxin while other commonly used laboratory animals do not. Mice housed at usual room temperature become hypothermic after injection of endotoxin but develop fever when housed at 30° C. See, e.g., page xx in the Introduction in *Cellular Biology of Endotoxin*, L. Berry ed., Volume 3 in the series *Handbook of Endotoxin* (R. Proctor, series ed.) Elsevier, Amsterdam, 1985.

Of interest to the background of the invention are numerous reports concerning the in vivo effects of administration of endotoxin to healthy human volunteers. Martich et al., *Immunobiol.*, 187:403–416 (1993) provides a current and detailed review of the literature addressing the effects on circulatory system constituents brought about by experimental endotoxemia in otherwise healthy humans. Noting that the responses initiated by endotoxin in humans are common to the acute inflammatory response that is part of the host reaction to tissue injury or infection, the authors maintain that administration of endotoxin serves as a unique means of evaluating inflammatory responses as well as responses specific to endotoxin. The authors also note that, while administration of endotoxin to healthy humans is not a precise model for the entirety of host responses in septic shock, it does allow investigation of the initial host inflammatory response to bacterial endotoxin.

Martich et al. note that intravenous administration of endotoxin is uniformly accompanied by a febrile response and various constitutional changes (myalgia and the like) which are attenuated by ibuprofen but not by the phosphodiesterase inhibitor, pentoxifylline. Cardiovascular responses qualitatively similar to those observed in clinical sepsis are observed in experimental endotoxemia in humans. Characteristic increases are observed in circulating cytokines such as tumor necrosis factor α (TNF), interleukin 6 (IL-6); interleukin 1β (IL-1β), interleukin 8 (IL-8), and granulocyte colony stimulating factor (GCSF). Inhibitory soluble receptors of TNF were also noted to rise in a characteristic pattern following increases in levels of circulating TNF. The studies reported on in Martich et al. provided observations that ibuprofen increased levels of circulating TNF and IL-6 in experimental endotoxemia and that pentoxifylline decreased circulating TNF, but not circulating IL-6.

Human experimental endotoxemia was noted to give rise to humoral inflammatory responses similar to those observed in sepsis. The fibrinolytic system is activated and levels of tissue plasminogen activator (tPA) in circulation rise, accompanied by increases in α2-plasmin inhibitor-plasmin complexes (PAP), confirming activation of plasminogen by tPA. Endotoxin administration to humans has been observed to prompt transitory leukopenia followed by rapid leukocytosis. Neutrophil degranulation occurs with attendant release of elastase (measured as elastase/α1-antitrypsin (EAA) complexes) and lactoferrin into circulation.

Martich et al. conclude that endotoxin administration to humans represents an important model of acute inflammation which reproduces many of the inflammatory events that occur during sepsis and septic shock and provides a unique means of studying host responses to an important bacterial product.

Following publication of the Martich et al. review article, the same research group reported on a study of experimental endotoxemia wherein an attempt was made to ascertain whether endotoxin administration into circulation could give rise to increased cytokine levels in the lung as measured by broncheoalveolar lavage (BAL). Boujoukos et al., *J. Appl. Physiol.*, 74(6):3027–3033 (1993). Even when ibuprofen was co-administered to enhance endotoxin mediated levels of circulating TNF and IL-6 in humans, no increases in TNF, IL-6 or IL-8 levels were observed in BAL fluid, suggesting that cytokine responses to endotoxin in circulation were compartmentalized and did not directly involve lung tissue endothelia.

Studies of the cardiovascular disturbances in septic shock have established that shock is usually characterized by a high cardiac index (CI) and a low systemic vascular resistance index (SVRI). [Parker et al., *Crit. Care. Med.*, 15:923–929 (1987); Rackow et al., *Circ. Shock*, 22:11–22 (1987); and Parker et al., *Ann. Intern. Med.*, 100:483–490 (1984).] Of additional interest to the background of the invention are studies of experimental endotoxemia in humans which have demonstrated depression of myocardial contractility and diastolic dysfunction. [Suffredini et al., *N. Eng. J. Med.*, 321:280–287 (1989).]

Bactericidal/Permeability-Increasing protein (BPI) is a protein isolated from the granules of mammalian polymorphonuclear neutrophils (PMNs), which are blood cells essential in the defense against invading microorganisms. Human BPI protein isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)] has optimal bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.*, 264:9505 (1989), incorporated herein by reference.

The bactericidal effect of BPI has been shown in the scientific literature published to date to be highly specific to sensitive gram-negative species, with toxicity generally lacking for other microorganisms and for eukaryotic cells. The precise mechanism by which BPI kills bacteria is not yet completely elucidated, but it is known that BPI must first attach to the surface of susceptible gram-negative bacteria. This initial binding of BPI to the bacteria involves electrostatic and hydrophobic interactions between the basic BPI protein and negatively charged sites on endotoxin. BPI binds to lipid A, the most toxic and most biologically active component of endotoxins.

In susceptible bacteria, BPI binding is thought to disrupt lipopolysaccharide (LPS) structure, leading to activation of bacterial enzymes that degrade phospholipids and peptidoglycans, altering the permeability of the cell's outer membrane, and initiating events that ultimately lead to cell death. [Elsbach and Weiss, *Inflammation: Basic Principles and Clinical Correlates*, eds. Gallin et al., Chapter 30, Reven Press, Ltd. (1992)]. BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by growth in serum albumin supplemented media. The second stage, defined by growth inhibition that cannot be reversed by serum albumin, occurs after a prolonged exposure of the bacteria to BPI and is characterized by extensive physiologic and structural changes, including penetration of the cytoplasmic membrane.

Permeabilization of the bacterial cell envelope to hydrophobic probes such as actinomycin D is rapid and depends upon initial binding of BPI to endotoxin, leading to organizational changes which probably result from binding to the anionic groups in the KDO region of endotoxin, which normally stabilize the outer membrane through binding of $Mg^{++}$ and $Ca^{++}$. Binding of BPI and subsequent bacterial killing depends, at least in part, upon the endotoxin polysaccharide chain length, with long O chain bearing organisms being more resistant to BPI bactericidal effects than short, "rough" organisms [Weiss et al., *J. Clin. Invest.*, 65:619–628 (1980)]. This first stage of BPI action is reversible upon dissociation of the BPI from its binding site. This process requires synthesis of new LPS and the presence of rivalent cations [Weiss et al., *J. Immunol.*, 132:3109–3115 (1984)].

Loss of bacterial viability, however, is not reversed by processes which restore the outer membrane integrity, suggesting that the bactericidal action is mediated by additional lesions induced in the target organism and which may be situated at the cytoplasmic membrane [Mannion et al., *J. Clin. Invest.*, 86:631–641 (1990)]. Specific investigation of this possibility has shown that on a molar basis BPI is at least as inhibitory of cytoplasmic membrane vesicle function as polymyxin B [In't Veld et al., *Infection and Immunity*, 56:1203–1208 (1988)] but the exact mechanism has not yet been elucidated.

A proteolytic fragment corresponding to the N-terminal portion of human BPI holoprotein possesses essentialy all the bactericidal efficacy of the naturally-derived 55 kD human holoprotein. [Ooi et al., *J. Bio. Chem.*, 262:14891–14894 (1987)]. In contrast to the N-terminal portion, the C-terminal region of the isolated human BPI protein displays only slightly detectable anti-bacterial activity. [Ooi et al., *J. Exp. Med.*, 174:649 (1991).] A BPI N-terminal fragment, comprising approximately the first 199 amino acid residues of the human BPI holoprotein and referred to as "$rBPI_{23}$," has been produced by recombinant means as a 23 kD protein. [Gazzano-Santoro et al., *Infect. Immun.*, 60:4754–4761 (1992).]

Of additional interest to the present application are the disclosures of references which relate to the potentialion of BPI bactericidal activity by 15 kD proteins derived from the granules of rabbit PMNs designated p15. Ooi et al., *J. Biol. Chem.*, 265:15956 (1990), disclose two related 15 kD proteins derived from rabbit PMN granules which potentiate the first sublethal stage of BPI antibacterial activity but have an inhibitory effect on the second lethal stage of BPI antibacterial activity. Levy et al., *J. Biol. Chem.*, 268:6058–6063 (1993), disclose the sequences of cDNAs encoding the two rabbit proteins and report that the protein with the stronger potentiating effect reduces the required dose of BPI for the early bacteriostatic effect by about 20-fold.

Of particular interest to the background of the present invention are reports of interaction between bacterial endotoxin and BPI protein products in various in vitro and non-human in vivo assay systems. As one example, Leach et al., Keystone Symposia "Recognition of Endotoxin in Biologic Systems", Lake Tahoe, Calif., Mar. 1–7, 1992 (Abstract) reported that $rBPI_{23}$ (as described in Gazzano-Santoro et al., supra) prevented lethal endotoxemia in actinomycin D-sensitized CD-1 mice challenged with *E. coli* 011:B4 LPS. In additional studies Kohn et al., *J. Infectious Diseases*, 168:1307–1310 (1993) demonstrated that $rBPI_{23}$ not only protected actinomycin-D sensitized mice in a dose-dependent manner from the lethal effects of LPS challenge but also attenuated the LPS-induced elevation of TNF and IL-1 in serum. Ammons et al., [*Circulatory Shock*, 41: 176–184 (1993)] demonstrated in a rat endotoxemia model that $rBPI_{23}$ produced a dose-dependent inhibition of hemodynamic changes associated with endotoxemia. Kelly et al., *Surgery*, 114: 140–146 (1993) showed that $rBPI_{23}$ conferred significantly greater protection from death than an antiendotoxin monoclonal antibody (E5) in mice innoculated intratracheally with a lethal dose of *E. coli*. Kung, et al., International Conference on Endotoxin Amsterdam IV, Aug. 17–20 (1993) (Abstract) disclosed the efficacy of $rBPI_{23}$ in several animal models including live bacterial challenge and endotoxemia models.

M. N. Marra and R. W. Scott and co-workers have addressed endotoxin interactions with BPI protein products in U.S. Pat. Nos. 5,089,274 and 5,171,739, in published PCT Application WO 92/03535 and in Matra et al., *J. Immunol.*, 144:662–665 (1990) and Marra et al., *J. Immunol.*, 148:532–537 (1992). In vitro and non-human in vivo experimental procedures reported in these documents include positive assessments of the ability of BPI-containing granulocyte extracts, highly purified granulocytic BPI and recombinant BPI to inhibit endotoxin stimulation of cultures of human adherent mononuclear cells to produce tumor necrosis factor α (TNF) when endotoxin is pre-incubated with the BPI product. Pre-incubation of endotoxin with BPI protein products was also shown to diminish the capacity of endotoxin to stimulate (upregulate) neutrophil cell surface expression of receptors for the complement system components C3b and C3bi in vitro. However, neither of these complement system components is known to have been demonstrated to be present in increased amounts in circulation as a result of the presence of endotoxin in human circulation. The experimental studies reported in these documents included in vivo assessments of endotoxin interaction with BPI protein products in test subject mice and rats. In one series of experiments, BPI was noted to inhibit stimulation of lung cell production of TNF (measured on the basis of cytotoxicity to fibrosarcoma cells of broncheoalveolar lavage fluids) in mice challenged by intranasal administration of endotoxin. In another series of experiments, administration of BPI was noted to protect mice and rats from lethal challenge with various bacterial endotoxin preparations and live Pseudomonas and binding of BPI to endotoxin was noted to diminish pyrogenicity in rabbits. As noted above, however, Boujoukas et al., *J. Appl. Physiol.*, 74(6):3027–3033 (1993) have demonstrated that, while administration of endotoxin to human circulation resulted in increased levels of circulating TNF, IL-6 and IL-8, no increases in these substances could be detected in broncheoalveolar lavage fluids of the human subjects.

Since the filing of parent U.S. patent application Ser. No. 08/188,221 on Jan. 24, 1994, additional studies of in vitro and in vivo effects of BPI have been published. Fisher et al., *Critical Care Med.*, 22(4):553–558 (1994) addressed studies in mice, rats and rabbits and concluded that, "The exciting possibility that bactericidal/permeability-increasing protein may be a specific therapeutic agent to enhance the natural negative feedback mechanisms for regulating endotoxin in humans is worth investigation." Marra et al., *Critical Care Med.*, 22(4):559–565 (1994) addressed studies in mice and concluded that, "The potent endotoxin-binding and -neutralizing properties of bactericidal/permeability-increasing protein indicate that it might be useful in the treatment of endotoxin-related disorders in humans."

Thus, while BPI protein products have been established to have potentially beneficial interactions with endotoxin in a variety of in vitro and non-human in vivo model systems, nothing is known concerning effects of these products in humans actually exposed to bacterial endotoxin in circulation as a result of, e.g., Gram negative bacterial infection, treatment with antibiotics, accidental injection with endotoxin-contaminated fluids, translocation of endotoxin from the gut, and the like.

SUMMARY OF THE INVENTION

The present invention provides novel methods for treatment of humans exposed to bacterial endotoxin in circulation involving the administration of BPI protein products to provide serologically, hematologically and hemodynamically verifiable alleviation of endotoxin effects. The invention thus addresses the use of BPI protein products in the manufacture of pharmaceutical compositions for the treatment of humans exposed to bacterial endotoxin in circulation.

According to one aspect of the invention, BPI protein products such as $rBPI_{23}$ are administered to humans in amounts sufficient to provide serologically, hematologically and hemodynamically verifiable alleviation of endotoxin mediated effects including, but not limited to: increases in circulating tumor necrosis factor (TNF), soluble TNF receptors p55 and p75 [sTNFr (p55) and sTNFr (p75)], interleukin 6 (IL-6), interleukin 8 (IL-8), interleukin 10 (IL-10) and increased neutrophil degranulation characterized by increased circulating lactoferrin and/or elastase/α1 antitrypsin complexes (EAA); increases in circulating tissue plasminogen activator antigen (tPA Ag), tissue plasminogen activator activity (tPA act), and α2-plasmin inhibitor-plasmin (PAP) complexes, plasminogen activator inhibitor antigen (PAI Ag) and urokinase type plasminogen activator (uPA); decreases in lymphocytes; increases in thrombin/antithrombin III (TAT) complexes; and decreases in systemic vascular resistance index (SVRI) and increases in cardiac index (CI).

According to another aspect of the invention BPI protein products are conjointly administered to human patients receiving antibiotic therapy to ameliorate, in a serologically, hematologically and hemodynamically verifiable manner, the effects of endotoxin release into circulation normally attending antibiotic mediated cytolysis or breakdown of bacteria.

In its presently preferred form, BPI protein products are administered according to the invention in dosage amounts of about 0.1 to about 10 mg/kg of body weight by parenteral, e.g., intravenous, routes in single and multiple dosage formats or by continuous infusion. Oral and aerosolized administration is also within the contemplation of the invention.

Other aspects and advantages of the present human treatment method inventions will be apparent to those skilled in the art upon consideration of the following detailed description of presently preferred embodiments thereof, reference being made to the drawing wherein data is presented for human patients exposed to bacterial endotoxin and either placebo-treated (open circles) or treated with a BPI protein product according to the invention (filled circles):

DETAILED DESCRIPTION

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; and biologically active polypeptide analogs of BPI protein or fragments or variants thereof, including cysteine-substituted analogs. The BPI protein products administered according to this invention may be generated and/or isolated by any means known in the art. U.S. Pat. No. 5,198,541, the disclosure of which is hereby incorporated by reference, discloses recombinant genes encoding and methods for expression of BPI proteins including recombinant BPI holoprotein, referred to as rBPI$_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 which are hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Figure 1:
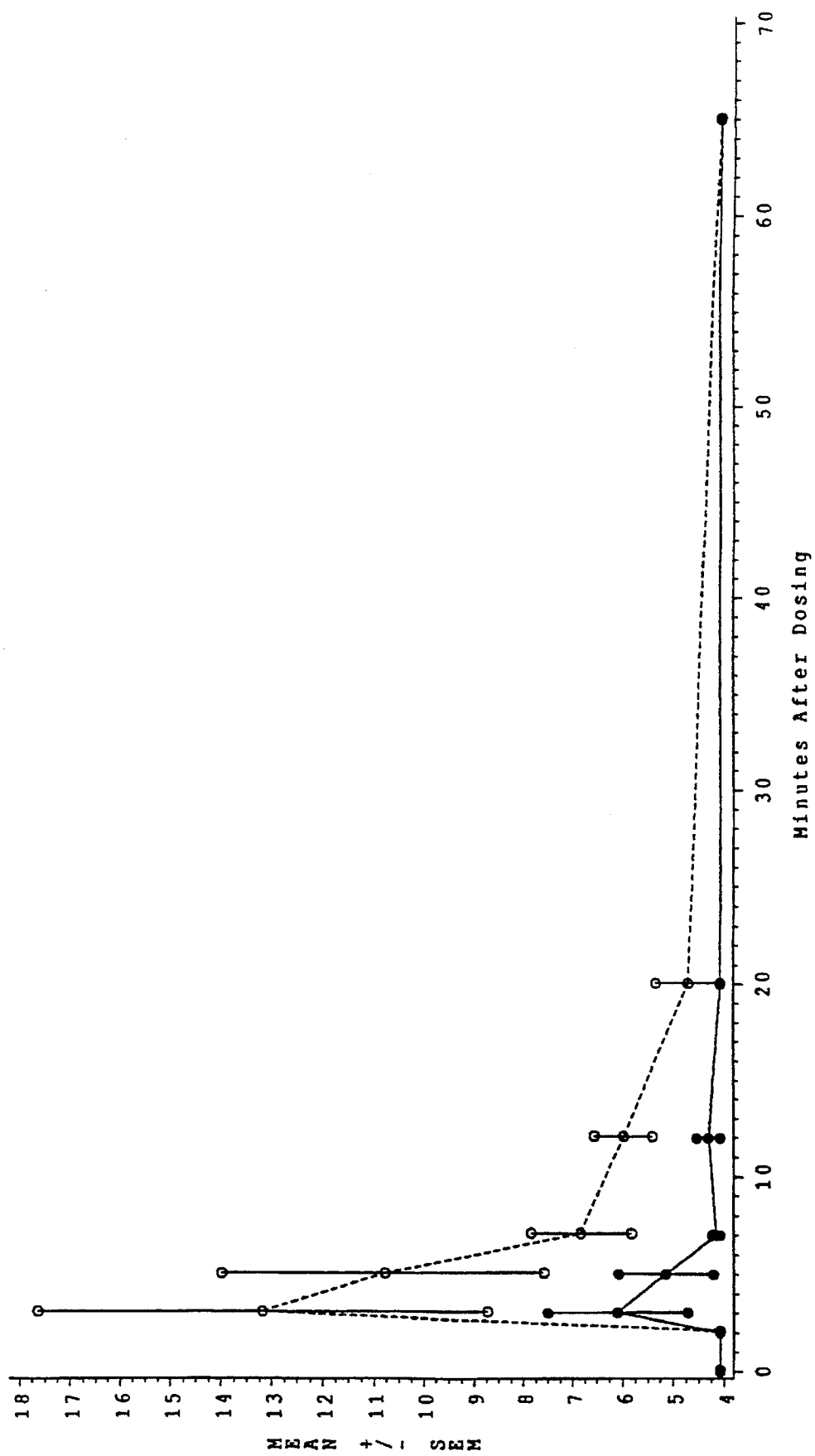
FIG. 1 is a graphic representation of the results of serological analysis for bacterial endotoxin.

Biologically active fragments of BPI (BPI fragments) include biologically active molecules that have the same amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ. ID NOS: 1 and 2) set out in FIG. 1 of Gray et al., supra, with the exceptions noted for rBPI$_{23}$ and with the exception that residue 417 is alanine (specified by GCT) rather than valine (specified by GTF). Other examples include dimeric forms of BPI fragments, as described in co-owned and co-pending U.S. patent application Ser. No. 08/212,132, filed Mar. 11, 1994, the disclosure of which is hereby incorporated by reference.

Biologically active variants of BPI (BPI variants) include but are not limited to recombinant hybrid fusion proteins, comprising BPI holoprotein or a biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof U.S. patent application Ser. No. 08/064,693 filed May 19, 1993 which are incorporated herein by reference in their entirety and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residue has been replaced by a different amino acid. For example, co-owned, copending U.S. patent application Ser. No. 08/013,801 (Theofan et al., "Stable Bactericidal/Permeability-Increasing Protein Products and Pharmaceutical Compositions Containing the Same," filed Feb. 2, 1993), the disclosure of which is incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI$_{21}$.

Other BPI protein products useful according to the methods of the invention are peptides derived from or based on BPI produced by recombinant or synthetic means (BPI-derived peptides), such as those described in co-owned and copending U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202, filed Jul. 15, 1993), which is a continuation-in-part of U.S. patent application Ser. No. 08/030,644, filed Mar. 12, 1993, the disclosures of which are hereby incorporated by reference. Other useful BPI protein products include peptides based on or derived from BPI which are described in co-owned and co-pending U.S. patent application Ser. No. 08/274,299, filed Jul. 11, 1994, by Horwitz et al. and U.S. patent application Ser. No. 08/273,540, filed Jul. 11, 1994, by Little et al.

Presently preferred BPI protein products include recombinantly-produced N-terminal fragments of BPI, especially those having a molecular weight of approximately between 21 to 25 kD such as rBPI$_{23}$ or rBPI$_{21}$ and dimeric forms of these N-terminal fragments. Additionally, preferred BPI protein products include rBPI$_{50}$ and BPI-derived peptides.

It is also contemplated that the BPI protein product be administered with other products that potentiate the activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.*, 265: 15956 (1990) and Levy et al. *J. Biol. Chem.*, 268: 6038–6083 (1993) which address naturally-occurring 15 kD proteins potentiating BPI antibacterial activity. See also co-owned, co-pending U.S. patent application Ser. No. 08/093,201, filed Jul. 14, 1993, and continuation-in-part, U.S. patent application Ser. No. 08/274,373, filed Jul. 11, 1994 which describes methods for potentiating gram-negative bactericidal activity of BPI protein products by administering lipopolysaccharide binding protein (LBP) and LBP protein products. The disclosures of these applications are incorporated by reference herein. LBP protein derivatives and derivative hybrids which lack CD-14 immunostimulatory properties are described in co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of which are incorporated by reference herein.

Practice of the methods of the present invention is illustrated in the following examples wherein: Example 1 presents the protocol for a controlled, double-blind crossover study of the effects of a BPI protein product on human volunteers challenged with bacterial endotoxin; Example 2 addresses serological analysis for cytokines and cytokine-related substances; Example 3 addresses lactose and glucose serological analysis; Example 4 addresses total and differential leukocyte analysis and leukocyte activation analysis; Example 5 addresses serological analysis of various coagulation and fibrinolysis parameters; and Example 6 addresses analysis of hemodynamic parameters, specifically left ventricular function.

EXAMPLE 1

A controlled, double-blind crossover study was designed to investigate the effects of BPI protein products (represented by the recombinant-produced amino terminal fragment referred to as $rBPI_{23}$) in humans rendered endotoxemic by intravenous infusion of bacterial endotoxin.

Eight healthy male volunteers participated in the study. Each had an unremarkable medical history, a normal physical exam and essentially normal results in routine laboratory tests. EKG, chest X-ray and echocardiogram results were within the normal range for all volunteers. Participation in the study was excluded if any infectious disease had occurred within one month prior to the study, if any acute illness was reported one week prior to the study or if any medication was taken within two weeks prior to the study. Written informed consent was obtained from all participants and the study was approved by an ethical review board. The study had a cross over design in which the subjects were challenged with endotoxin on two occasions, separated by a 6 week wash out period. Placebo or $rBPI_{23}$ was administered concurrently with endotoxin at either of the two occasions, so that each volunteer served as his own control. The treatment sequence ($rBPI_{23}$ followed by placebo, placebo followed by $rBPI_{23}$) was determined by randomization in a 1:1 ratio to the two sequences. Thus four volunteers were treated with $rBPI_{23}$ during the first cycle of endotoxin challenge, and four during the second cycle.

The study drug, $rBPI_{23}$, was prepared according to the method of Gazzano-Santoro et al., supra, and was supplied as a clear, colorless, sterile, non-pyrogenic solution in 10 ml single use glass vials at a concentration of 1 mg/ml in a buffer of 20 mmol/l sodium citrate, 0.15M sodium chloride, 0.1% poloxamer 188, 0.002% polysorbate 80, pH 5.0, containing no preservative. The placebo solution was supplied as a clear, colorless, sterile, non-pyrogenic solution in 10 ml single use glass vials. This solution contained 0.2 mg/ml human albumin in a buffer of 20 mmol/l sodium citrate, 0.15 mol/l sodium chloride, pH 5.0, containing no preservative. A treatment kit for each subject was coded according to the randomization schedule.

The endotoxin preparation used was FDA lot EC-5 (*Escherichia coli*), kindly provided by Dr. D. Hochstein (Bureau of Biologics, U.S. Food and Drug Administration, Bethesda, Md.). Before injection, the endotoxin preparation was reconstituted according to FDA directions, warmed to 37° C., vigorously shaken for 30 minutes, and diluted to the appropriate concentration in endotoxin-free saline. $rBPI_{23}$ or placebo were administered in exactly five minutes, in a forearm vein. Endotoxin was injected intravenously in one minute, in a forearm vein of the opposite arm, at a dose of 40 EU/kg during the third minute of the test drug infusion. Blood pressure and heart rate were monitored at 15 minute intervals using a dinamap device (Critikon, Tampa Fla.).

Blood was obtained through an indwelling intravenous catheter, at the following time points: −30, 3, 5, 7, 12, 20, 30, 35 minutes, 1, 1.5, 2, 3, 4, 6, 8, 10 and 12 hours. Blood was collected in Vacutainer tubes (Becton Dickinson, Rutherford, N.J.) containing acid titrate dextrose for the BPI determination, in pyrogen-free plastic tubes (Falcon 2063, Oxnard, Calif.) containing pyrogen-free heparin (Thromboliquine® Organon, Oss, Netherlands, final concentration 30 U/ml) for the endotoxin test, in tubes containing $K_3$-EDTA for leukocyte counts, and in siliconized Vacutainer tubes (Becton Dickinson) to which soybean trypsin inhibitor was added for the elastase/$\alpha_1$-antitrypsin complex, lactoferrin and C3a-desarg assays. Serum was prepared for all other tests by centrifugation of clotted blood for 20 minutes at 2000×g.

For each experimental assessment made, data were analyzed to determine both mean and median values and the associated standard errors. Results were plotted as a function of the relevant time period. Statistical significance of treatment difference was assessed for median values using the Wilcoxon signed rank test [Lehmann, Nonparametrics-Statistical Methods Based on Ranks, (Holden-Day, Inc., San Francisco, Calif. 1975)] on the percent change in trapezoidal area under the curve (AUC) for BPI protein product treatment relative to the AUC on placebo treatment for each volunteer. Percent change in AUC for $rBPI_{23}$ treatment relative to placebo was defined as $100 \times (AUC_{BPI} - AUC_{placebo})/(AUC_{placebo})$. A negative percent change implies a reduction in AUC for $rBPI_{23}$ treatment relative to placebo treatment. Statistical significance was assessed separately in each functional group of assays so that the type 1 error rate for each group of parameters was maintained at $\alpha=0.05$. The Hochberg method [Hochberg, *Biometrika*, 75:800–802 (1988)], an improved Bonferroni procedure [Miller, Simultaneous Statistical Inference (Springer-Verlag, New York, N.Y., second ed., 1981)] for multiple significance testing, was used to determine statistical significance within each group of parameters. Tests for carryover and period effects were performed according to the nonparametric method described by Koch, *Biometrics*, 28:577–584 (1972). Where period effects were observed by this method, treatment differences were further explored by performing the test for treatment effect in the presence of period effects as described in Koch, supra.

Infusion of rBPI$_{23}$ concomitantly with endotoxin resulted in a transient (15 minutes) flush in six of the eight volunteers, but caused no other signs. Following infusion of endotoxin, body temperature rose similarly after placebo or BPI infusion. The mean arterial blood pressure decreased in both study periods, and was not influenced by the BPI infusion. No safety related EKG changes were noted in any of the volunteers. Volunteers suffered from clinical symptoms such as headache, myalgia, chills and nausea in both treatment regimens. All volunteers were completely recovered at 24 hours following the start of the infusion, and renal, liver and hematological parameters were within the normal range at this time point.

Vital sign parameters including systolic blood pressure (SBP), diastolic blood pressure (DPP), mean arterial pressure (MAP), pulse, respiration rate and temperature were assessed. Table 1, below, sets out the results of statistical analysis of vital signs and reveals that there was no statistically significant difference in values for the rBPI$_{23}$-treated patients relative to placebo patients.

TABLE 1

VITAL SIGNS

| Parameter | AUC hours | Median % change in AUC | p-value[a] | Statistical significance[b] |
|---|---|---|---|---|
| DBP | 0–10 | −1% | .95 | NS |
| MAP | 0–10 | +1% | .74 | NS |
| Resp Rate | 0–10 | −6% | .64 | NS |
| SBP | 0–10 | +3% | .55 | NS |
| Temp | 0–10 | −4% | .1094 | NS |
| Pulse | 0–10 | −21% | .0391 | NS |

[a]p-value comparing rBPI$_{23}$ vs. placebo AUC within each subject (Wilcoxon signed rank test).
[b]Statistical significance as determined by the Hochberg method (S = significant, NS = nonsignificant).

Endotoxin assays were performed as described in van Deventer et al., *Blood*, 76(12):2520–2526 (1990). Results are graphically represented in FIG. 1 wherein mean values±standard error of the mean for placebo-treated patients are represented by open circles and values for BPI treated patients are represented by filled circles. Over the period of zero time to 20 minutes, endotoxin levels were significantly higher following placebo treatment in comparison to rBPI$_{23}$ treatment (Median percent change in AUC= 98%; p-value=0.0156).

EXAMPLE 2

Cytokine and Cytokine Related Proteins

Serum levels of TNF were determined by immunoradiometric assay IRMA Medgenix, Fleurus, Belgium). Briefly noted, polypropylene tubes were coated with a combination of monoclonal antibodies to recombinant TNF that recognize distinct epitopes of TNF. The tubes were incubated overnight with a mixture of the sample to be tested and anti-TNF antibody labeled with $^{125}$I. After decantation, the bound fraction was counted in a gamma-counter, and the level of TNF was expressed in pg/ml in relation to a standard binding curve for recombinant TNF.

The serum concentrations of IL-1β, IL-8 and IL-10 were performed by a commercial ELISA kit according to the instructions of the manufacturer (Medgenix, Fleurus, Belgium). Serum concentration of IL-6 was also determined by ELISA according to manufacturer's instructions. [Central Laboratory of the Netherlands Red Cross Blood Transfusion Service (CLB) Amsterdam, Netherlands].

Soluble TNF receptor p55 and p75 concentrations were measured by specific enzyme linked immunological assays as described in Nujens et al., *J. Lab. Clin. Med.*, 119:159–168 (1992). Briefly, microtiter plates (Maxisorp, Nunc, Denmark) were coated overnight at room temperature with TNF-binding non-inhibitory monoclonal antibodies against TNFR-p55 (clone htr-20) or TNFR-p75 (clone utr-4), kindly provided by Dr. H. Gallati, Hoffmann LaRoche Ltd., Basel, Switzerland. Subsequently, the coated wells were washed and the remaining protein-binding capacity of the wells was saturated with 1% BSA in 200 mM Tris/HCl, pH 7.5, 0.02% kathon. After discarding the storage buffer, samples diluted 1:5 in 0.1M Tween 20, pH 7.25, containing 10% fetal bovine serum, 0.1% phenol, 0.1% Tween 20, 0.02% kathon were added to the wells. Standard curves were constructed with recombinant sTNFR-p55 or sTNFR-p75. Peroxidase-conjugated recombinant human TNF was added and the mixtures were incubated for two days at 4° C. After washing, ortho-phenyldiaminedihydrochloride substrate was added and incubated for 15–20 min. The reaction was stopped with 1.5M H$_2$SO$_4$ and the absorbance was spectrophotometrically determined at 490 nm.

Figure 2:
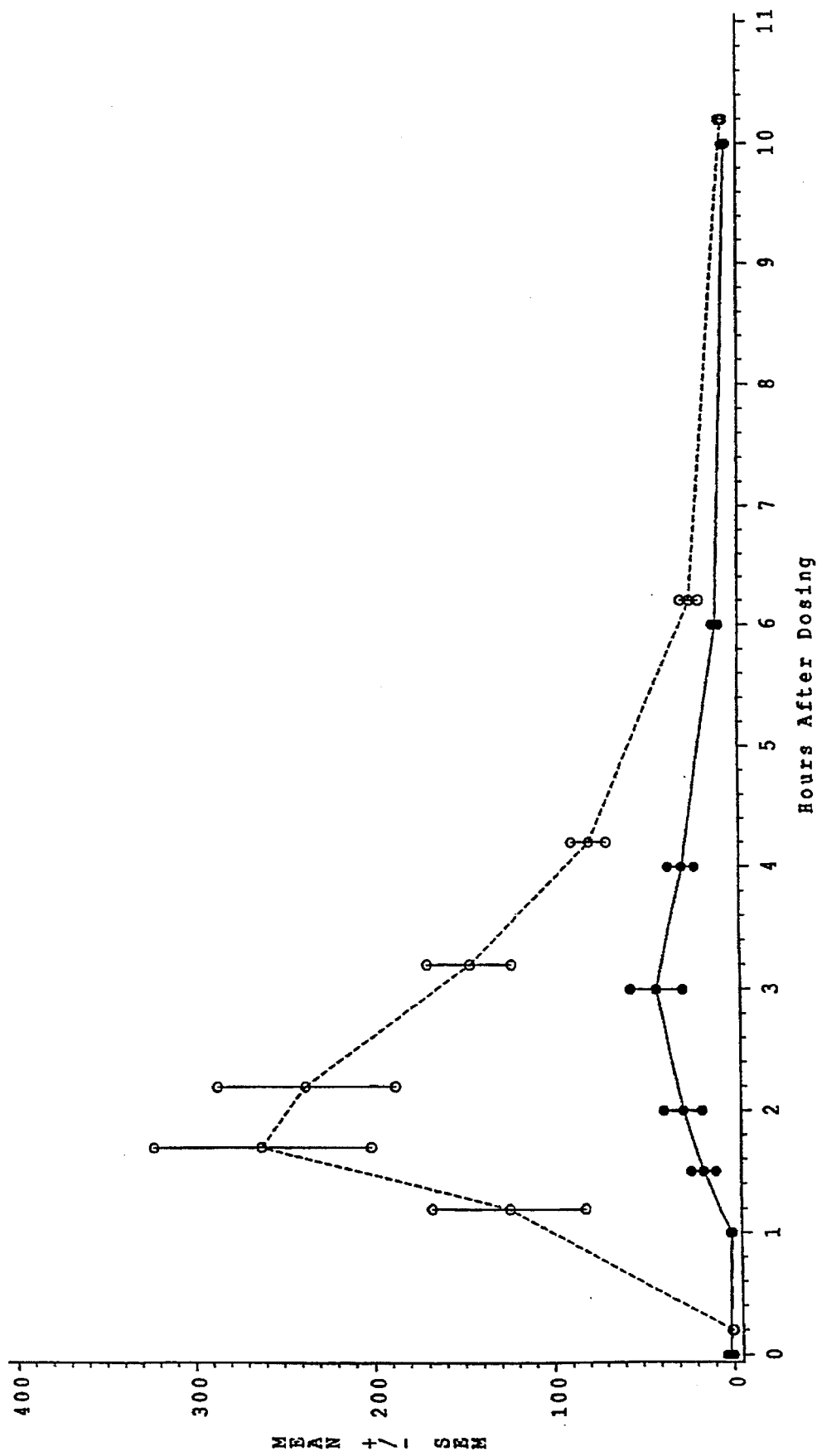
FIG. 2 is a graphic representation of the results of serological analysis for TNF.
Figure 3:
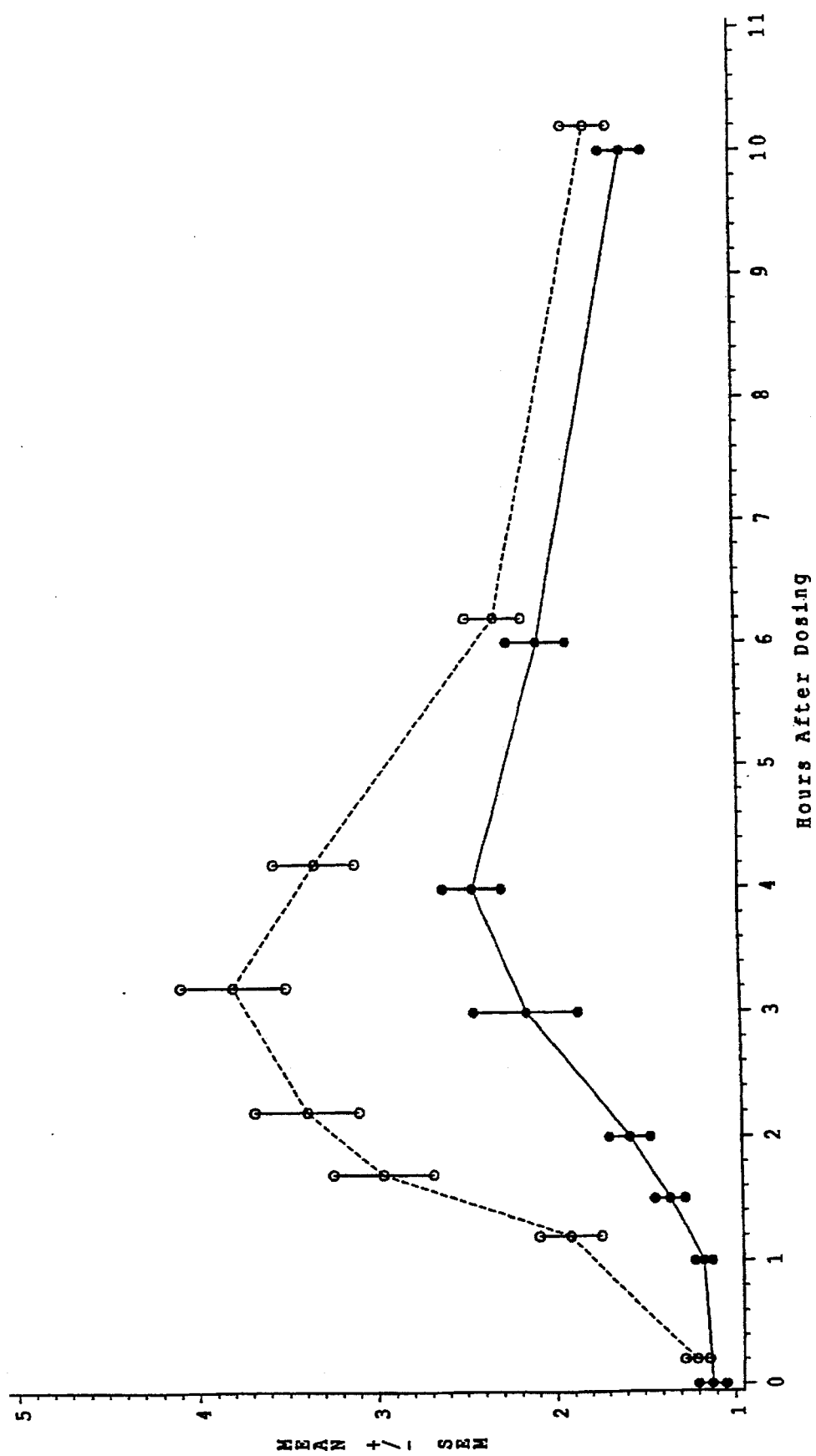
FIG. 3 is a graphic representation of the results of serological analysis for soluble TNF p55 receptor.
Figure 4:
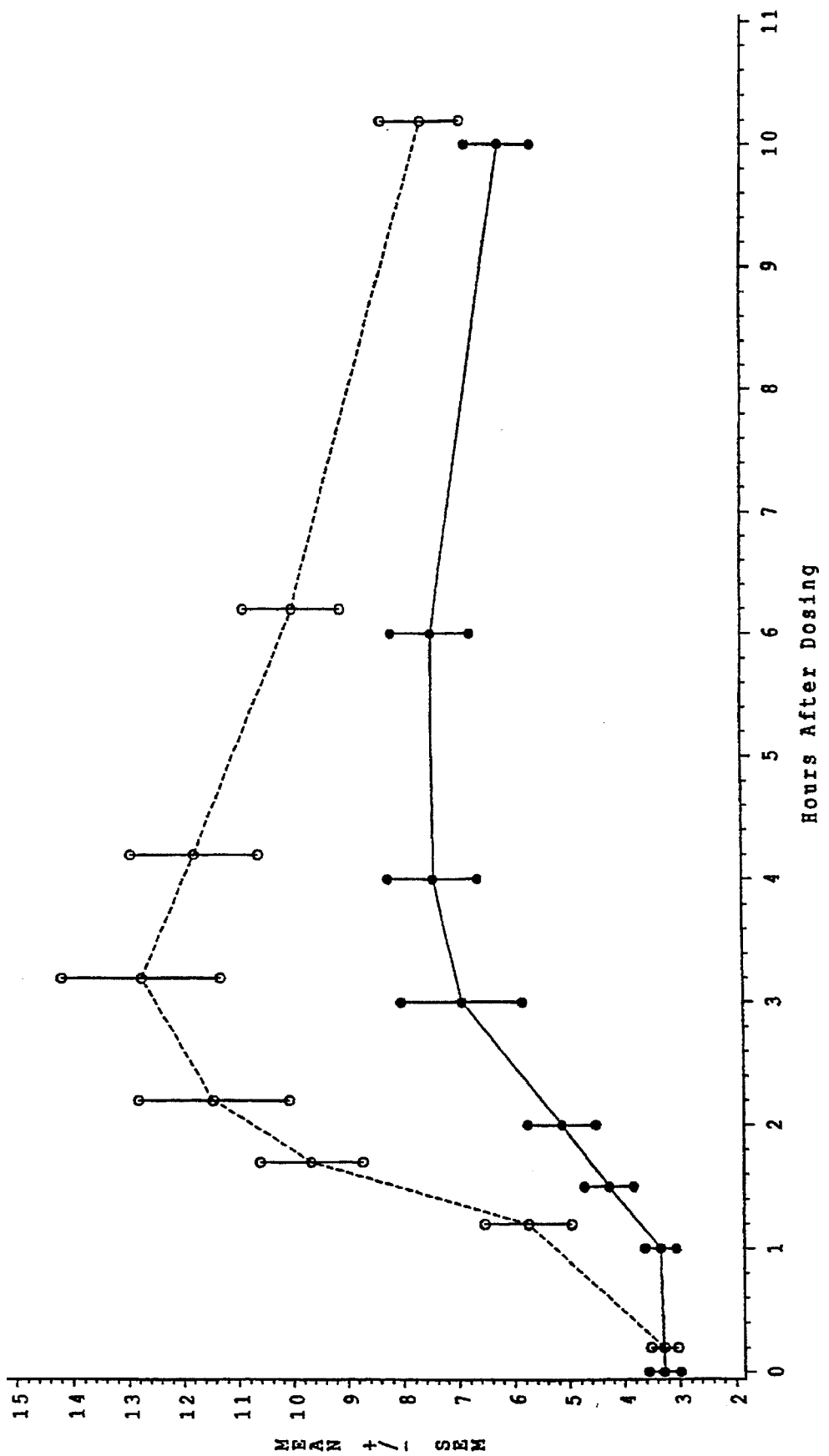
FIG. 4 is a graphic representation of the results of serological analysis for soluble TNF p75 receptor.

Assay results for TNF and the p55 and p75 soluble TNF receptors are graphically presented in FIGS. 2, 3 and 4, respectively. As indicated therein, TNF levels increased following endotoxin/placebo infusion from 0.50±0.38 pg/ml (mean±SEM) immediately prior to infusion to peak levels of 261.88±60.73 pg/ml at one and one half hours and returned to 3.50±0.91 pg/ml by ten hours. When endotoxin infusion was accompanied by rBPI$_{23}$, however, the TNF peak was blunted (41.13±14.36 pg/ml) and delayed to three hours after infusion. The serum concentrations of both types of TNF receptors were elevated after endotoxin/placebo challenge but increased to a lesser extent following endotoxin infusion with rBPI$_{23}$ and peak levels were temporally shifted.

Post-treatment IL-1 levels were below the assay detection limit during the entire experiment in both treatment periods.

Figure 5:
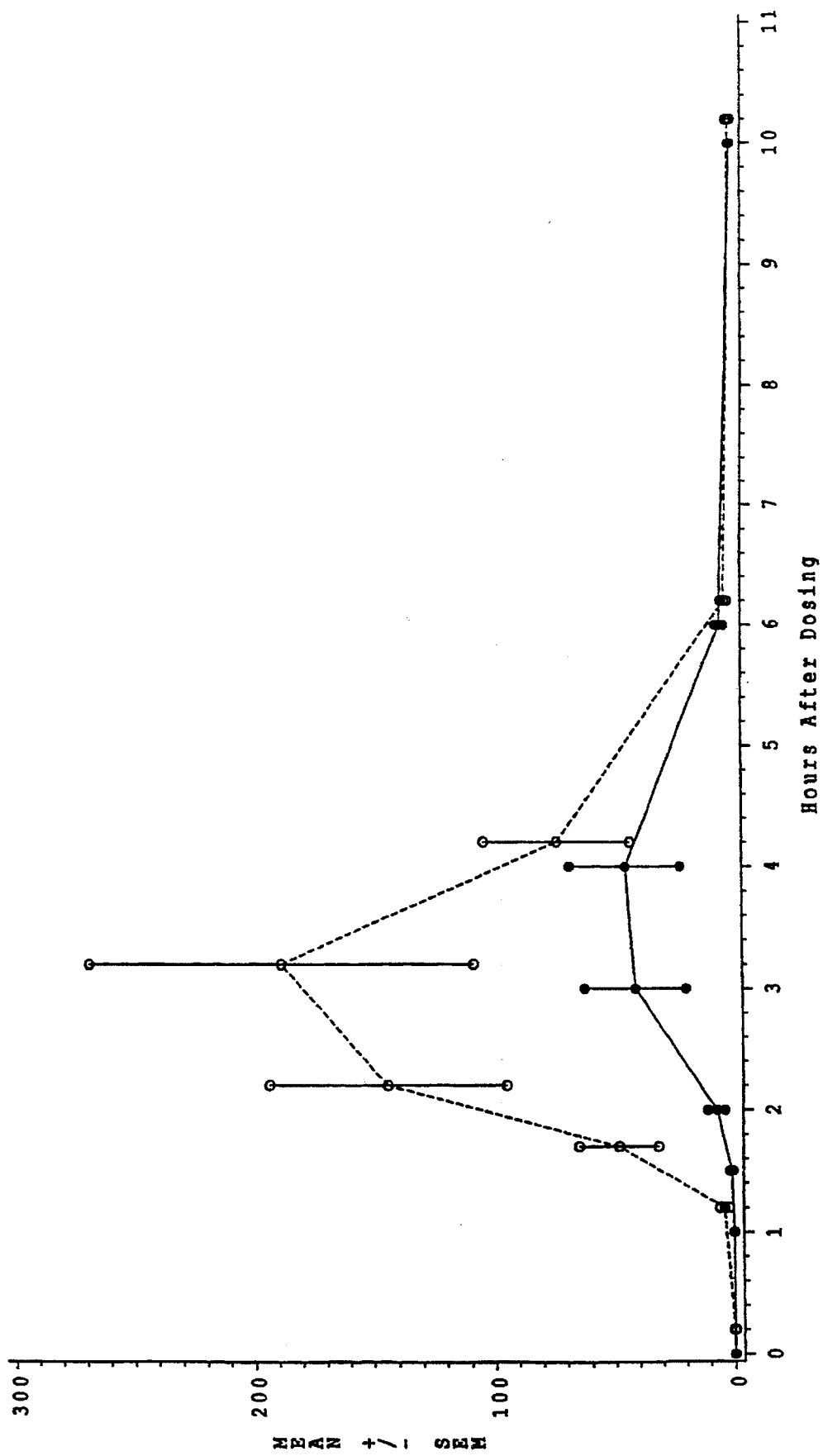
FIG. 5 is a graphic representation of the results of serological analysis for IL-6.

As indicated in FIG. 5, in endotoxin/placebo treated volunteers IL-6 levels increased from 0.23±0.23 pg/ml (mean±SEM) prior to infusion to 188.78±79.99 pg/ml at three hours and returned to normal values at 10 hours. After rBPI$_{23}$ treatment, IL-6 rose from 0.06±0.04 pg/ml prior to infusion to reach peak levels of 45.13±23.28 pg/ml at 4 hours and subsequently returned to normal at 10 hours.

Figure 6:
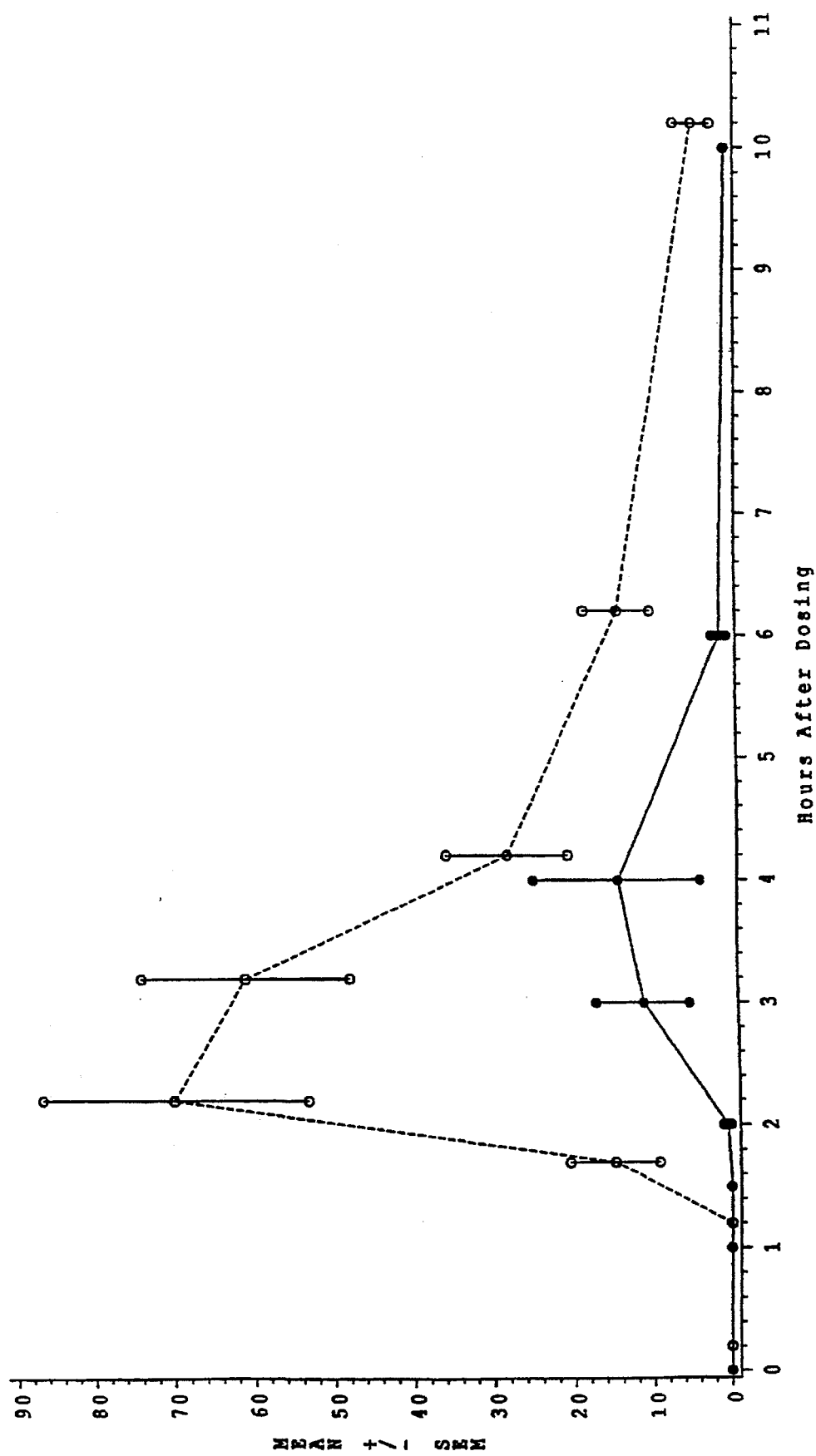
FIG. 6 is a graphic representation of the results of serological analysis for IL-8.

As indicated in FIG. 6, IL-8 increased from undetectable levels prior to infusion to 69.83±16.72 pg/ml (mean±SEM) at two hours in endotoxin/placebo treated patients and decreased again to 4.18±2.38 pg/ml at 10 hours following endotoxin infusion. After rBPI$_{23}$ infusion the IL-8 peak occurred later (14.20±10.63 pg/ml at four hours) and IL-8 levels remained undetectable throughout the entire ten hour assessment period in three out of eight volunteers. At 10 hours, no IL-8 was detectable in any volunteer receiving rBPI$_{23}$.

Figure 7:
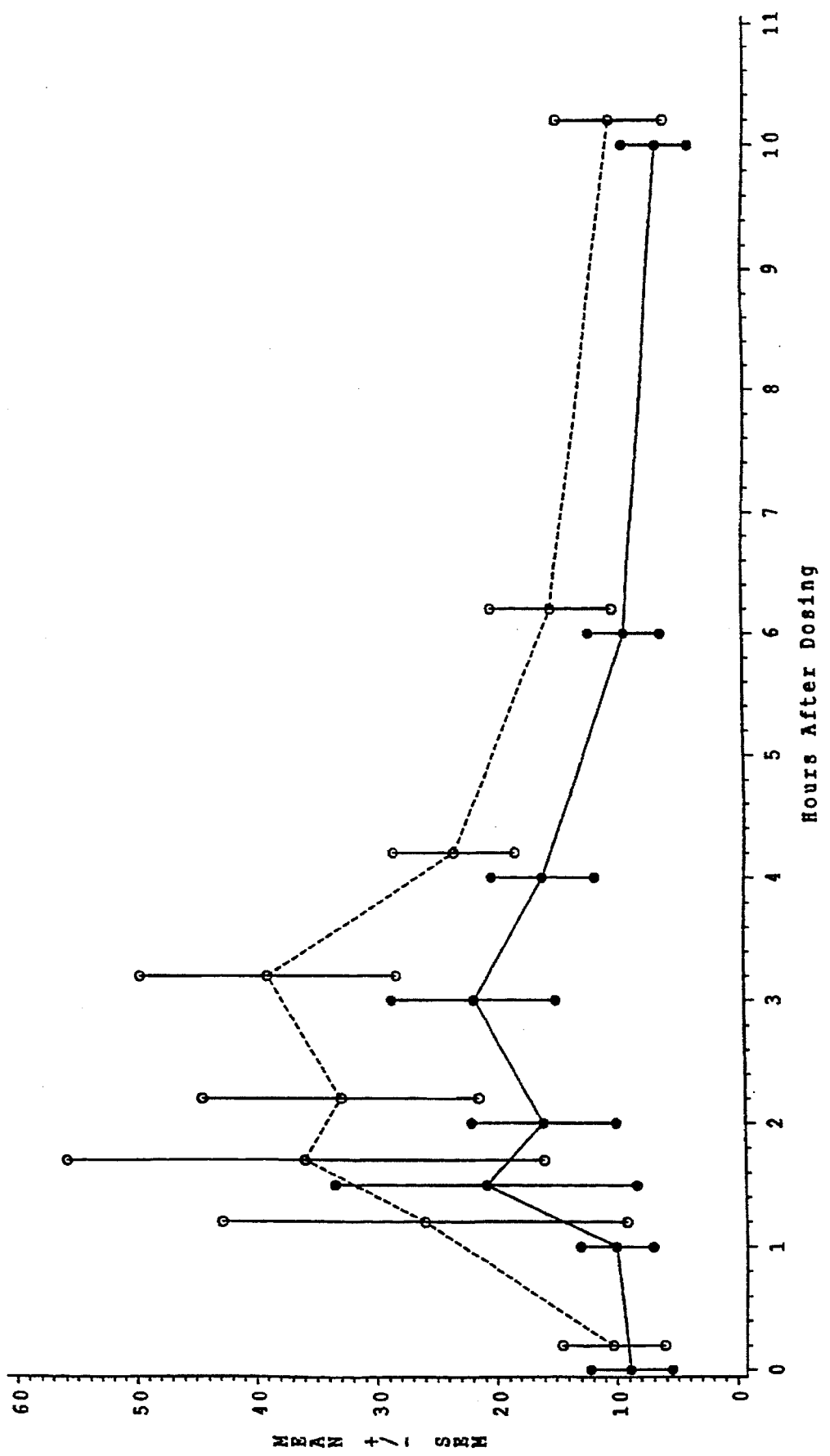
FIG. 7 is a graphic representation of the results of serological analysis for IL-10.

Serum levels of IL-10 increased in endotoxin challenged volunteers after both placebo and rBPI$_{23}$ treatment. As seen in FIG. 7, peak levels were observed between one and one-half to three hours after infusion. In the placebo group, IL-10 rose from 10.35±4.19 pg/ml (mean±SEM) prior to infusion to 38.94±10.66 pg/ml (at three hours) and declined to 10.35±4.37 pg/ml (at ten hours). In the rBPI$_{23}$ treated group, IL-10 was increased to a lesser extent; i.e., from an initial level of 8.86±3.35 pg/ml to 21.76±6.89 pg/ml at three hours.

Table 2, below, sets out the results of statistical analysis of test results for cytokines and cytokine related proteins from time 0 through ten hours.

TABLE 2

CYTOKINES AND CYTOKINE RELATED PROTEINS

| Parameter | AUC hours | Median % change in AUC | p-value[a] | Statistical significance[b] |
|---|---|---|---|---|
| IL-1 | 0–10 | 0% | .25 | NS |
| IL-10 | 0–10 | −38% | .0156 | S |
| IL-6 | 0–10 | −79% | .0078 | S |
| IL-8 | 0–10 | −97% | .0078 | S |
| TNF | 0–10 | −86% | .0078 | S |
| TNF r(p55) | 0–10 | −40% | .0078 | S |
| TNF r(p75) | 0–10 | −48% | .0078 | S |

[a]p-value comparing rBPI$_{23}$ vs. placebo AUC within each subject (Wilcoxon signed rank test).
[b]Statistical significance as determined by the Hochberg method (S = significant, NS = nonsignificant).

The above results establish that treatment of experimental endotoxemia in humans with a BPI protein product resulted in a serologically verifiable and statistically significant modification in cytokine response to the presence of endotoxin in circulation. The severity and temporal setting of TNF production mediated by endotoxin was dramatically altered and was accompanied by corresponding decreases in levels of circulating soluble TNF receptors and a temporal shifting of peak circulating receptor values. In a like manner, the presence of IL-6 in circulation as a consequence of endotoxin in circulation was significantly modified. While one previous study indicated that circulating TNF levels in experimental endotoxemia in humans could be diminished by intervention with pentoxifylline [Zabel et al., Lancet, 2:1474–1477 (1989)], and ibuprofen has been observed to increase TNF and IL-6 levels following endotoxin administration, no previous study of this type has identified an agent which is effective in reducing TNF and IL-6 responses to endotoxin in humans.

Reduction in TNF response to endotoxin through administration of rBPI was accompanied not only by reductions in circulating TNF receptors but also reduction in circulating IL-10, a substance which has been characterized as an anti-inflammatory cytokine. The reduction and shifting in peak IL-8 levels attending is the subject of discussion in Example 4, infra.

EXAMPLE 3

Lactate and Glucose Analysis

Lactate and glucose analyses were performed using standard laboratory procedures. Briefly summarized, serum glucose rose similarly over time in both treatment groups, while in each group there was only a slight rise from baseline levels of lactate.

EXAMPLE 4

Total and Differential Leukocytes and Leukocyte Activation Analysis

Figure 10:
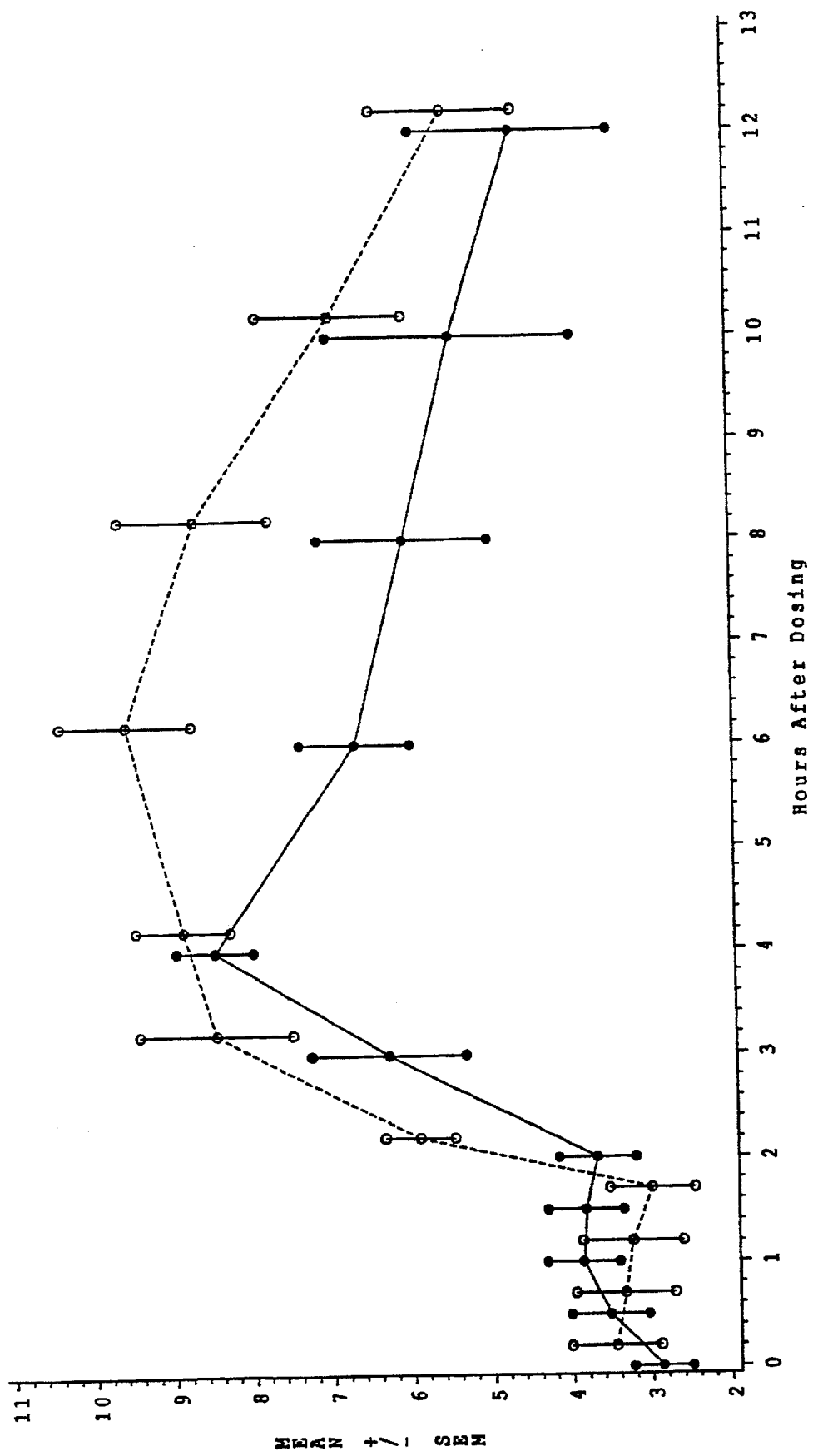
FIG. 10 is a graphic representation of the results of hematological analysis for neutrophils.
Figure 11:
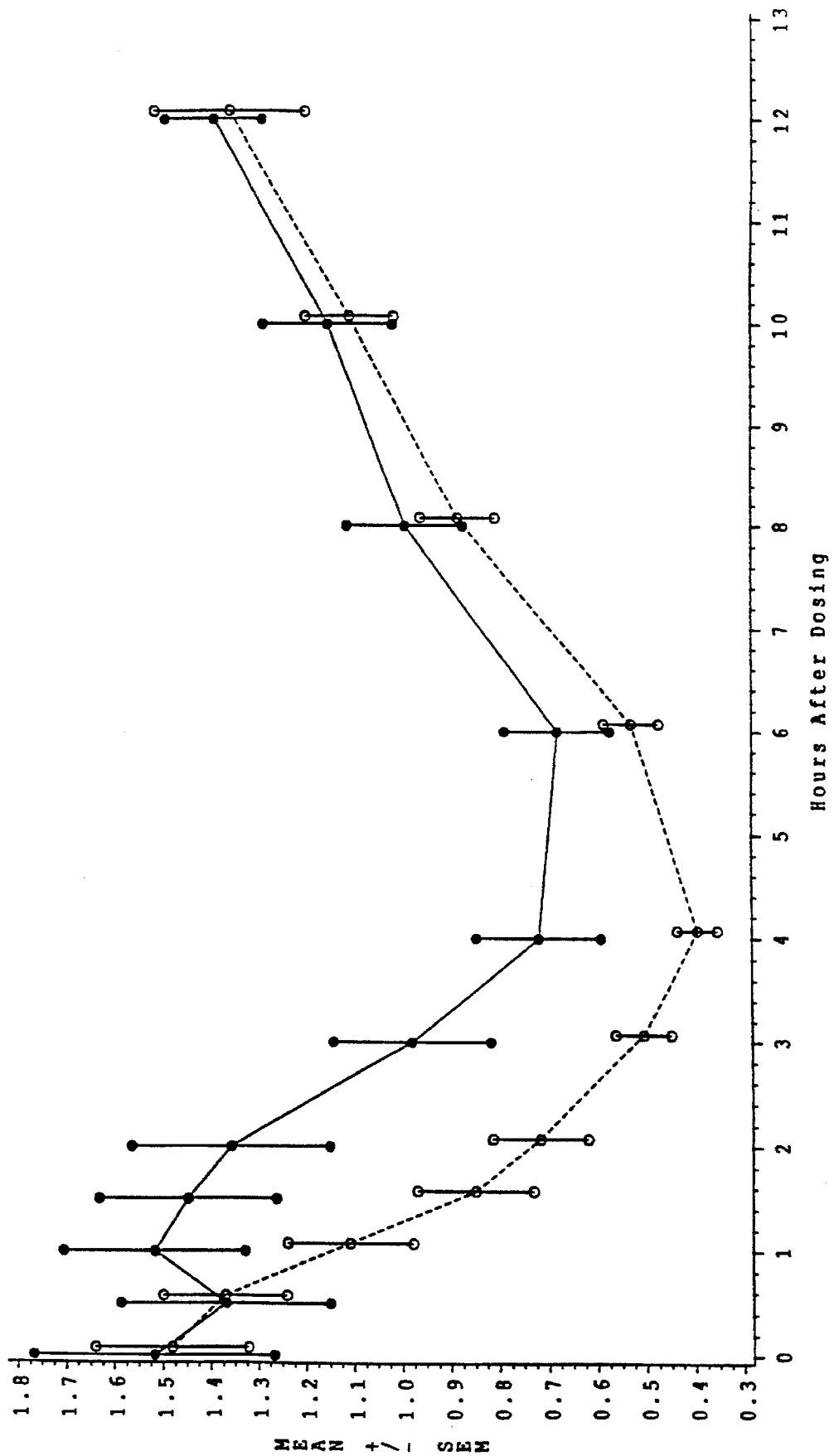
FIG. 11 is a graphic representation of the results of hematological analysis for lymphocytes.
Figure 12:
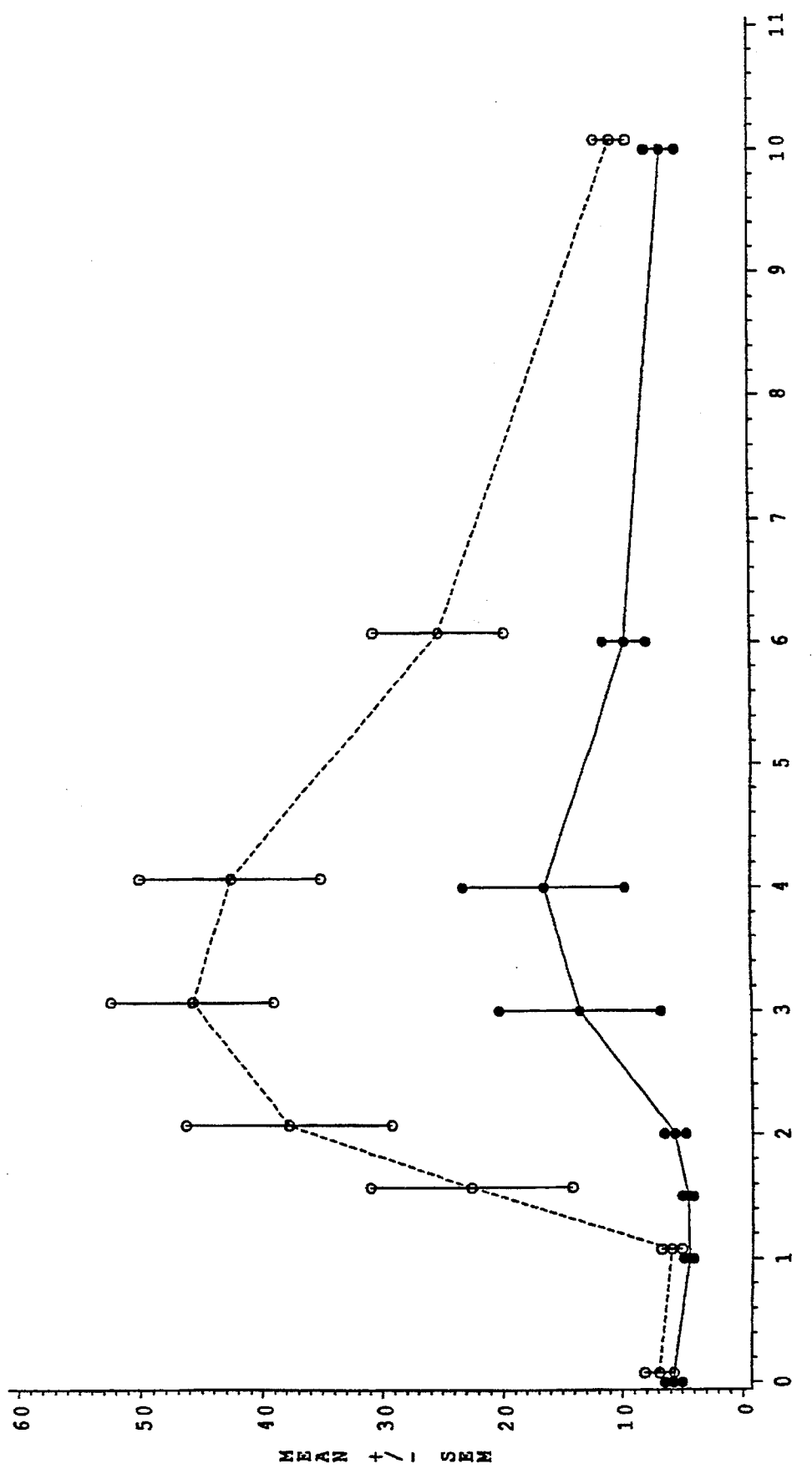
FIG. 12 is a graphic representation of the results of serological analysis for tissue plasminogen activator antigen.
Figure 13:
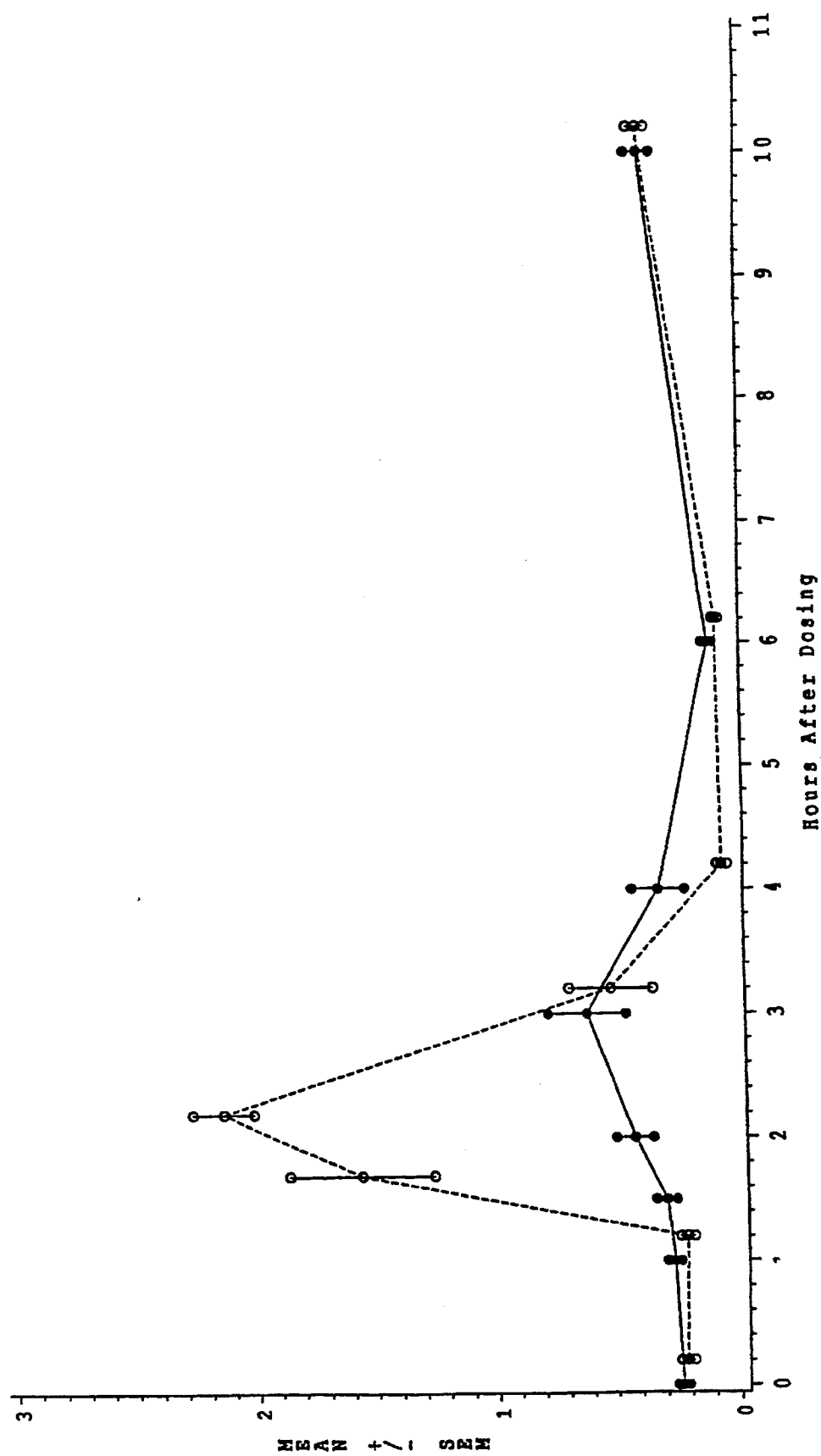
FIG. 13 is a graphic representation of the results of serological analysis for tissue plasminogen activator activity.
Figure 14:
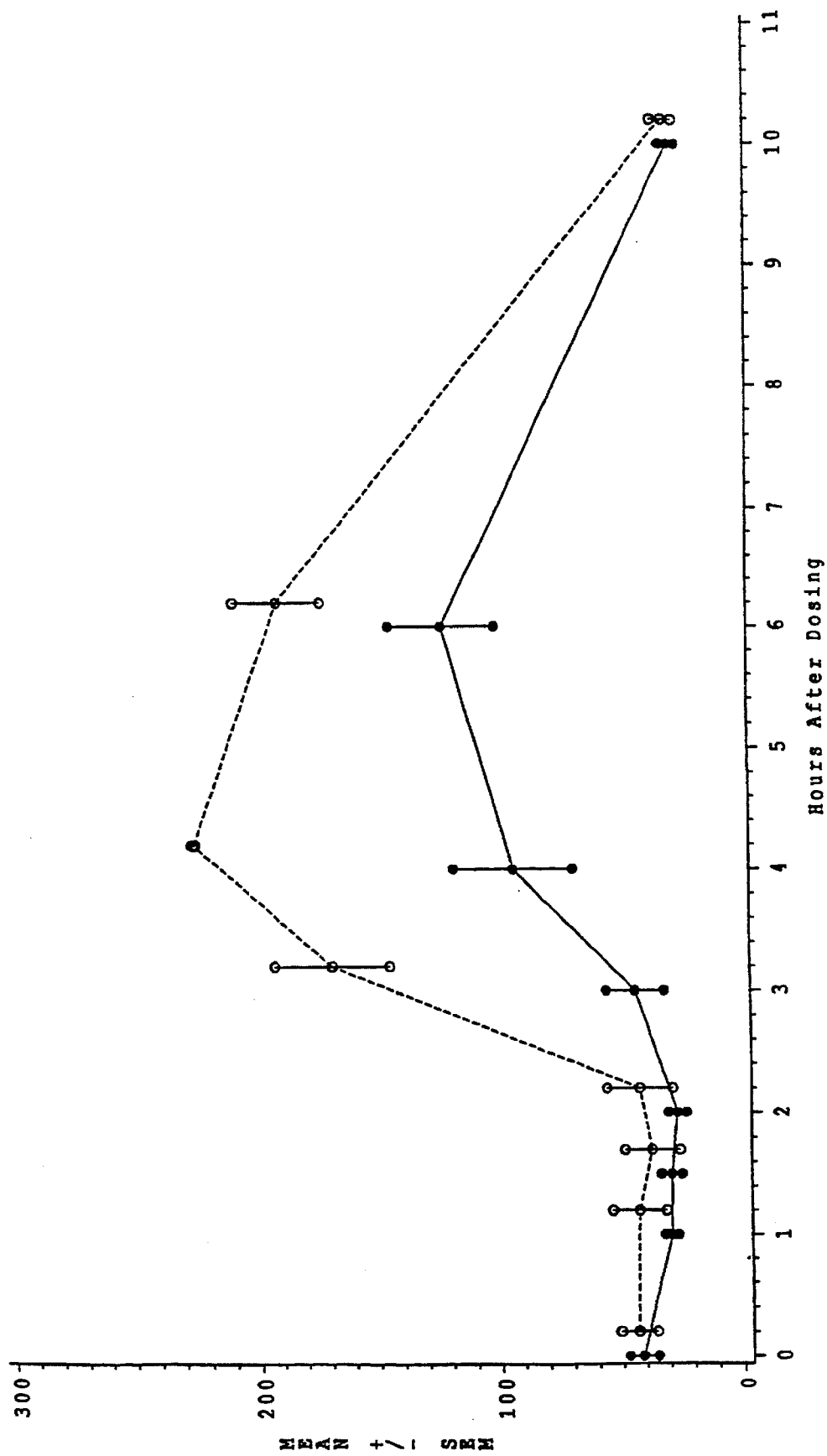
FIG. 14 is a graphic representation of the results of serological analysis for plasminogen activator inhibitor antigen.
Figure 15:
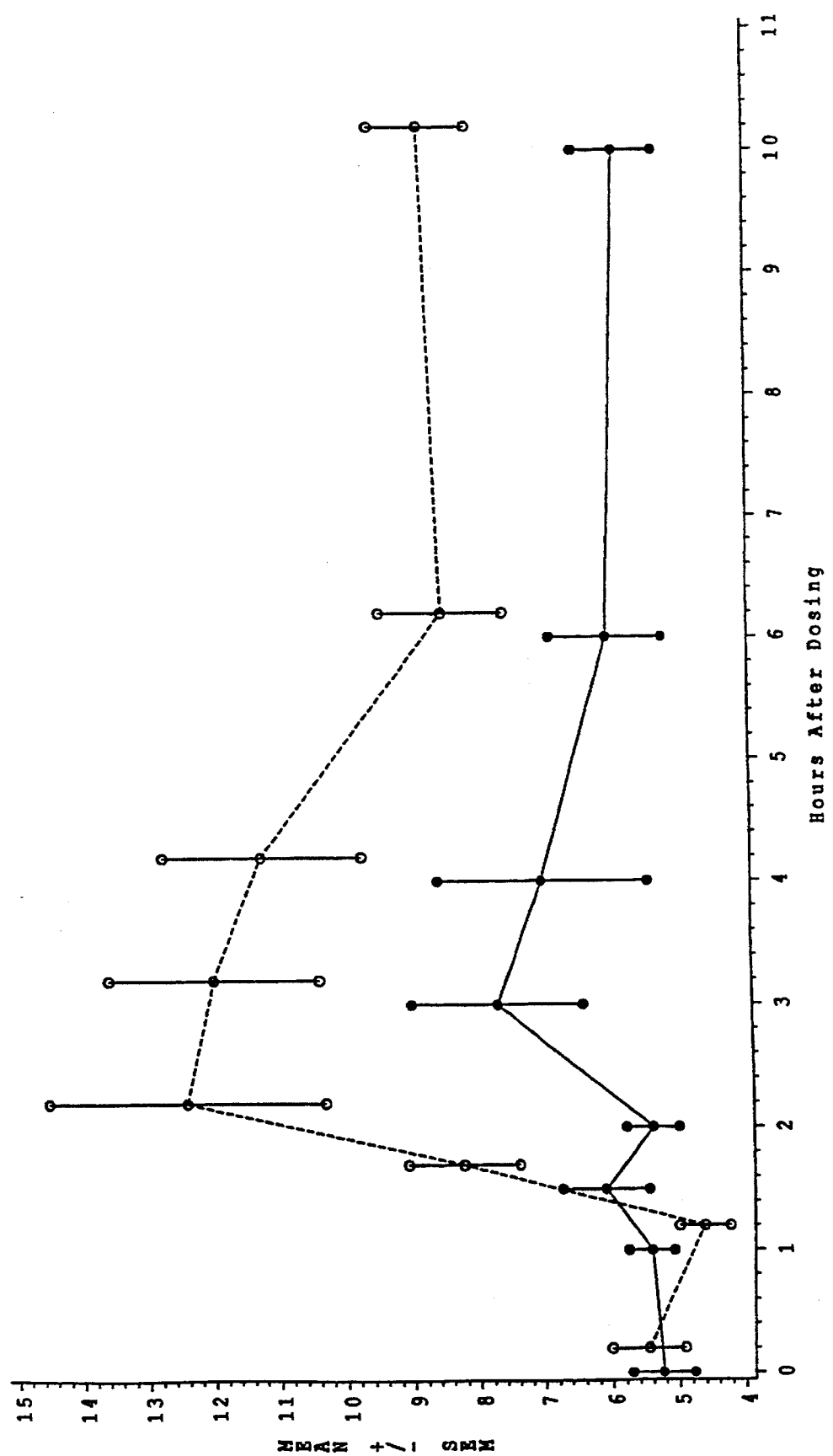
FIG. 15 is a graphic representation of the results of serological analysis for α2-plasmin inhibitor-plasmin complexes.
Figure 16:
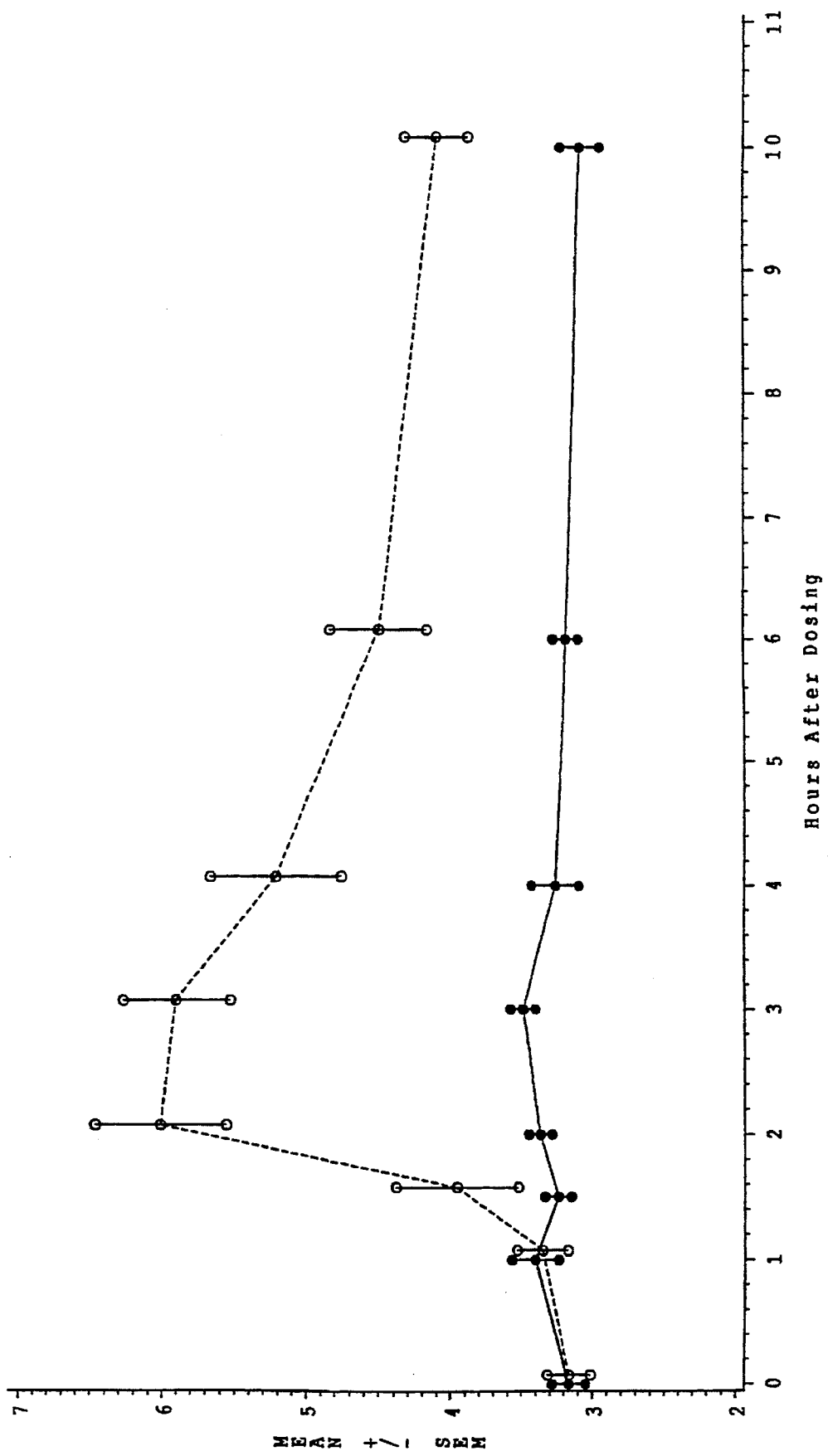
FIG. 16 is a graphic representation of the results of serological analysis for urokinase type plasminogen activator.
Figure 17:
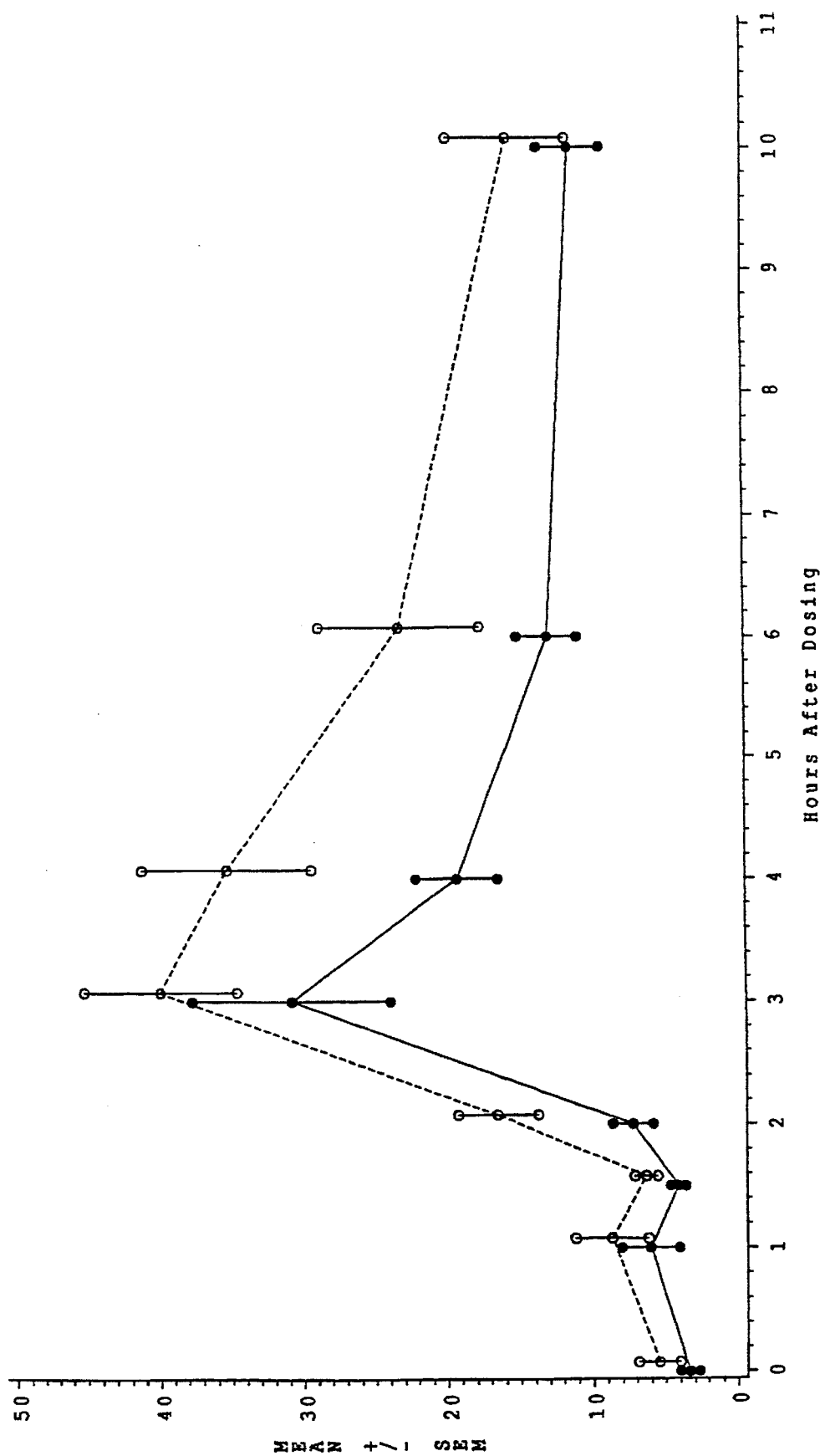
FIG. 17 is a graphic representation of the results of serological analysis for thrombin/antithrombin III (TAT) complexes.

Leukocyte total and differential counts were determined through use of a flow cytometer (Technicon H1 system, Technicon Instruments, Tarrytown, N.Y.). Results for neutrophil and lymphocyte determinations (mean±SEM) are also set out in graphic form in FIGS. 10 and 11, respectively. Placebo treated volunteers displayed a characteristic transitory drop in neutrophils followed by a sharp rise in the neutrophil count. See, e.g., van Deventer et al., Blood, 76:2520–2526 (1990). Treatment with rBPI$_{23}$ blunted both phases of the endoxotin effect.

Table 3, below, sets out the results of statistical analysis of total and differential leukocytes from time 0 through 10 hours.

TABLE 3

| | LEUKOCYTE DIFFERENTIAL | | | |
|---|---|---|---|---|
| Parameter | AUC hours | Median % change in AUC | p-value[a] | Statistical significance[b] |
| Basophils | 0–12 | +2% | .95 | NS |
| Eosinophils | 0–12 | +37% | .0391 | NS |
| WBC | 0–12 | −19% | .0391 | NS |
| Monocytes | 0–12 | +42% | .0234 | NS |
| Neutrophils | 0–12 | −26% | .0156 | NS |
| Lymphocytes | 0–12 | +34% | .0078 | S |

[a]p-value comparing rBPI$_{23}$ vs. placebo AUC within each subject (Wilcoxon signed rank test).
[b]Statistical significance as determined by the Hochberg method (S = significant, NS = nonsignificant).

Plasma concentrations of elastase/α1-antitrypsin complex (EAA) and lactoferrin were measured by radioimmunoassay according to the method described in Nuijens et al., supra, and values determined in terms of ng/ml. Complement activation was assessed by measuring the plasma concentrations of C3a-desarg using a radioimmunoassay as described in Hack et al., J. Immunol. Meth., 107:7784 (1988) and values were expressed in terms of nmol/l.

Figure 8:
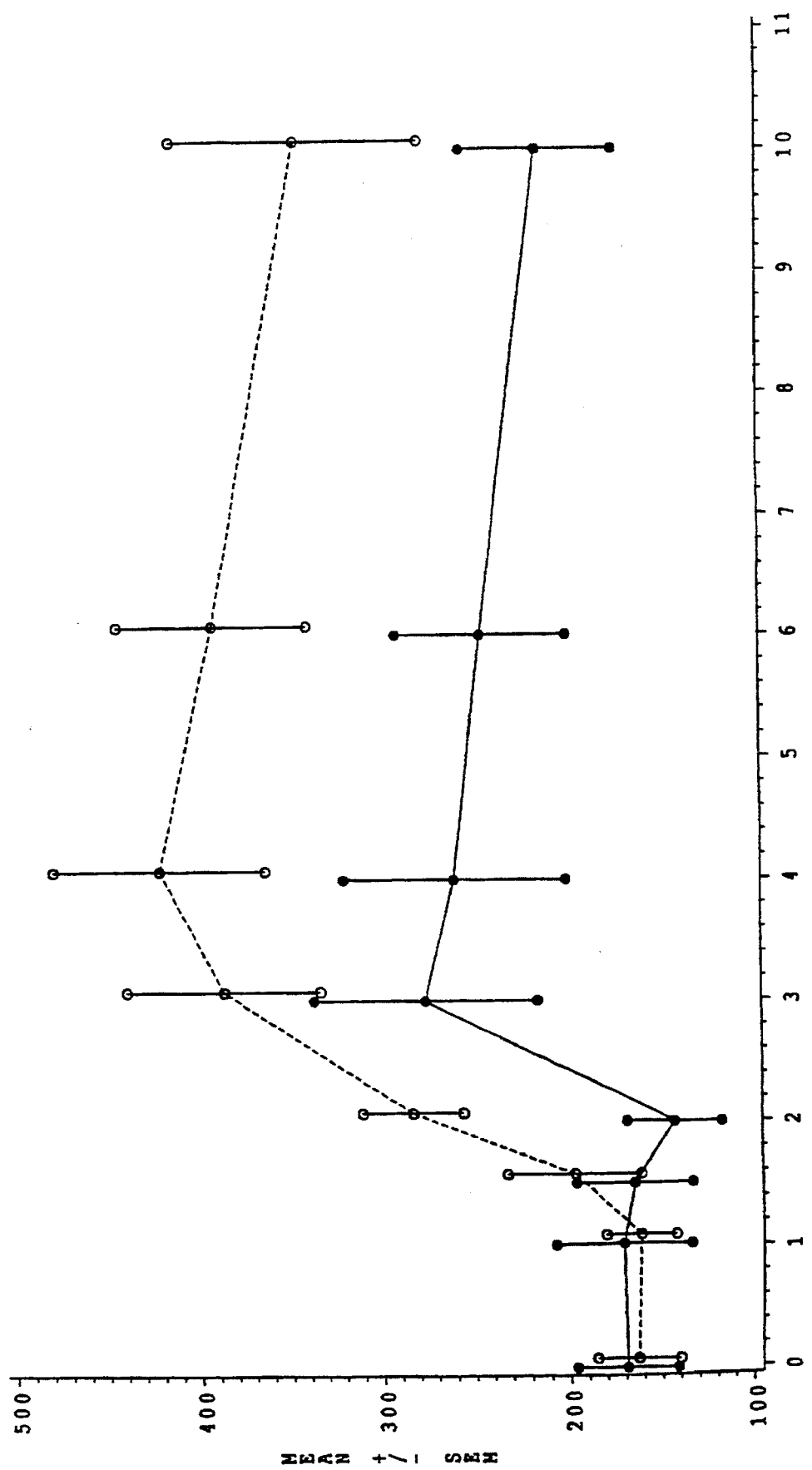
FIG. 8 is a graphic representation of the results of serological analysis for lactoferrin.
Figure 9:
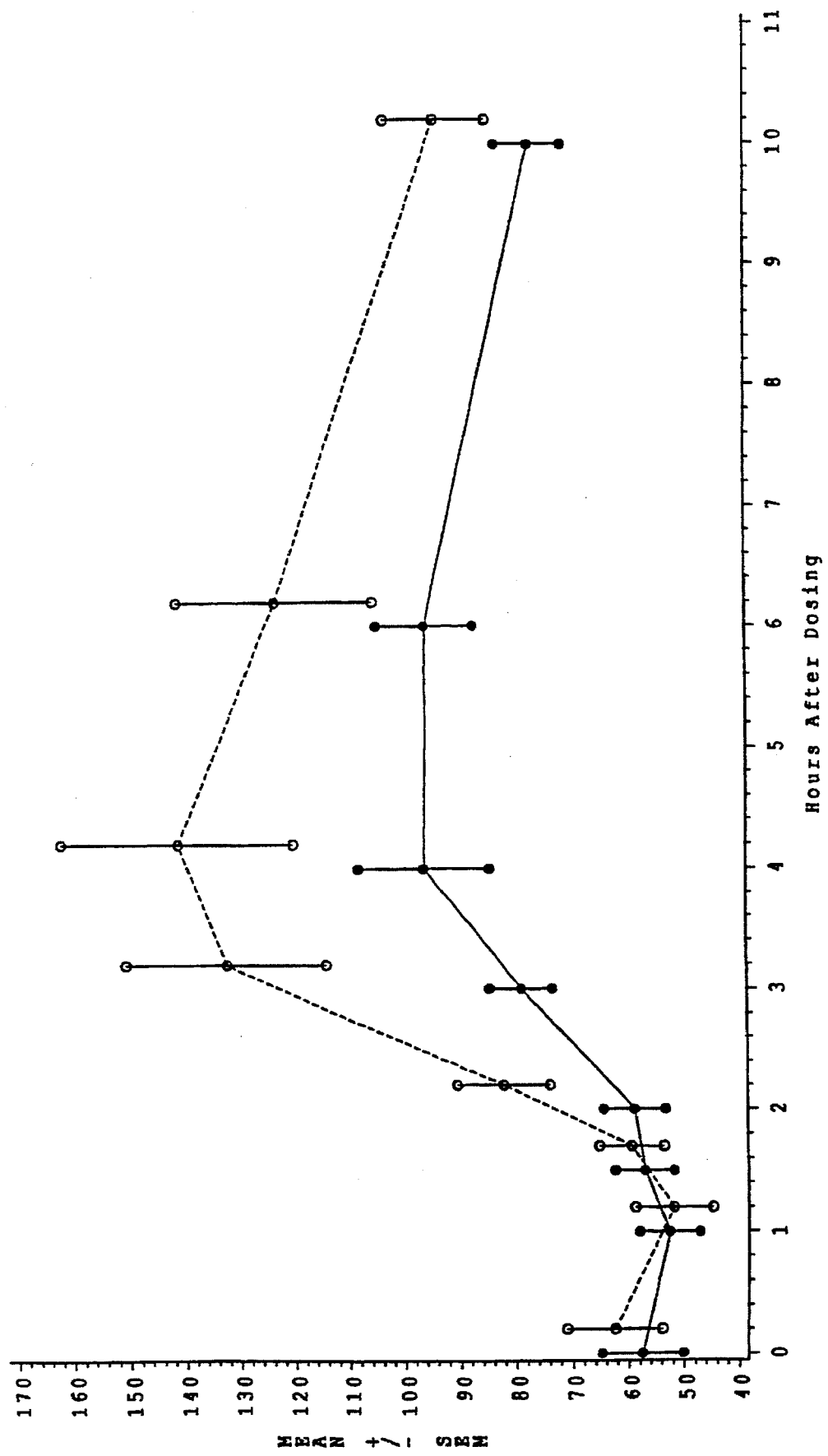
FIG. 9 is a graphic representation of the results of serological analysis for elastase/α1 antitrypsin complexes.

Lactoferrin and EAA analysis results are set out in Table 4 below and mean±SEM results also graphically represented in FIGS. 8 and 9, respectively.

TABLE 4

| | LEUKOCYTE ACTIVATION | | | |
|---|---|---|---|---|
| Parameter | AUC hours | Median % change in AUC | p-value[a] | Statistical significance[b] |
| EAA | 0–10 | −36% | .0304[c] | S |
| Lactoferrin | 0–10 | −47% | .0078 | S |

[a]p-value comparing rBPI$_{23}$ vs. placebo AUC within each subject (Wilcoxon signed rank test).
[b]Statistical significance as determined by the Hochberg method (S = significant, NS = nonsignificant).
[c]Accounting for period effect.

While no significant differences in C3a-desarg were noted for the two treatment strategies, in BPI-treated volunteers EAA complex formation and lactoferrin assay results were markedly lower than in placebo-treated volunteers. The results observed in the EAA and lactoferrin assays are consistent with the previously noted reduction in IL-8 values in BPI-treated individuals. IL-8 has been implicated in effecting degranulation of neutrophils and rises in lactoferrin and EAA in circulation result from neutrophil degranulation. Thus, the present study reflects the first known instances of intervention in experimental endotoxemia in humans resulting in reduction of circulating levels of endotoxin mediated IL-8 and a coordinated reduction of neutrophil degranulation as assessed by analysis of circulating lactoferrin and EAA.

EXAMPLE 5

Fibrinolysis and Coagulation Parameter Analysis

Serological analyses were performed to assess circulating levels of D-dimer, prothrombin fragments F1+2 (Frag F1+2), plasminogen activator inhibitor antigen (PAI Ag), plasminogen activator inhibitor activity (PAI Act), α2-plasmin inhibitor-plasmin complexes (PAP), protein C activity (Prot. C Act), thrombin-antithrombin III (TAT) complex, α2-antiplasmin (AAP), plasminogen, tissue plasminogen activator antigen (tPA Ag), tissue plasminogen activator activity (tPA Act) and urokinase type plasminogen activator (u PA). Blood was collected by separate venous punctures from antecubital veins, before and at 1, 1.5, 2, 3, 4, 6 and 10 hours after the start of the endotoxin infusion. Blood for AAP, plasminogen, tPA Ag, uPA, PAI Ag, PAI Aer, D-dimer, Prot. C Act, Frag F1+2 and TAT complex measurements (9 volumes) was collected in vacutainer tubes (Becton Dickinson, Rutherford, N.J.) containing 3.8% sodium citrate (1 volume). Blood for t-PA Act was collected in Biopool Stabilyte™ tubes (Biopool, Umea, Sweden) containing a low pH citrate anticoagulant which stabilizes t-PA activity by blocking inhibition of t-PA of PAI. For the measurements of PAP complexes, blood was collected in siliconized vacutainer tubes (Becton Dickinson, Plymouth, England) to which EDTA (10 mM, final concentration) and Soy Bean Trypsin Inhibitor (Sigma T-9003) was added to prevent in vitro complex formation. Tubes containing $K_3$-EDTA were used to collect blood for platelet counts. For all measurements except platelet counts, plasma was prepared by centrifuging at 2000×g for 30 minutes at 15 °C., after which plasma was frozen at −70° C. until batchwise assessment was performed.

Platelet counts were determined with the use of a flow cytometer (Technicon H1 system, Technicon Instruments, Tarrytown, U.S.A.), plasma levels of TAT complexes and of Frag F1+2 were measured with ELISA's (Behringwerke AG, Marburg, Germany) [Teitel et al., Blood, 59: 1086–1096 (1982)]. Protein C activity was measured by an amidolytic assay, as described in Sturk et al., Clin. Chim Acta, 165: 263–270 (1987). tPA Act was measured by an amidolytical assay [Verheijen et al., Thromb. Haemostasis, 48: 266–269 (1982)]. Briefly, 25 µl of plasma was mixed to a final volume of 250 µl with 0.1M Tris HCl, pH 7.5, 0.1% (v/v) Tween-80, 0.3 mM S-2251 (Kabi Haematology, M olndal, Sweden), 0.13M plasminogea and 0.12 mg/ml CNBr fragments of fibrinogen (Kabi Haematology, Mölndal, Sweden). The results are expressed as IU/ml (first international standard of the World Health Organization).

PAI Act was measured with an amidolytical assay [Chmielewska, et al., Thromb. Res., 31: 427–436 (1983)] in which the sample as were inculcated for 10 min at room temperature with an excess of tissue-type plasminogen activator. Part of the t-PA was inhibited by PAI, present in the sample, and formed inactive complexes. Residual t-PA activity was determined by subsequent incubation, with 0.13 µM plasminogen (Kabi Haematology), 0.12 mg/ml cyanogen bromide-digested fibrinogen fragments (t-PA stimulator, Kabi Haematology) and 0.1 mM S-2251 (Kabi Haematology). The amount of plasmin generated in the incubation mixture, determined by the conversion of the chromogenic substrate, was inversely proportional to the PAI Act in the sample. The results of the samples to be tested were related to the results of samples of PAI Act depleted plasma (Kabi Haematology) to which fixed amounts of t-PA were added. Results were expressed in international units (IU), where 1 IU is the amount of PAI Act that inhibits 1 IU t-PA.

t-PA Ag and PAI Ag were assayed with ELISA's [Holvoer et al., Thromb. Haemostasis, 54: 684 (1985)] (Asserachrom t-PA, Diagnostica Stago, Asnieres-sur-Seine, France and PAI-ELISA kit, monozyme, Charlottenlund, Denmark respectively). Results are expressed in ng/ml. uPA was measured with a sandwich-ELISA [Binnema et al., Thromb. Res., 43: 569 (1986)]. The assay measures the urokinase-antigen present in plasma, irrespective of its molecular form i.e. pro-urokinase, active urokinase and urokinase in complex with inhibitors; the results are expressed in ng/ml. Plasminogen activity and AAP were measured by automated amidolytic techniques according to methods described in Peeters et al., Thromb. Res., 28: 773 (1982). The results are expressed as percentages of normal. D-Dimer was measured with an ELISA (Asserachrom D-Di, Diagnosfica Stago, Asnieres-sur Seine, France) [Elms et al., Thromb. Haemostasis, 50: 591 (1983)]. Results are expressed in µg/ml. PAP complexes were measured by a RIA as described in Levi et al., J. Clin. Invest. 88: 1155–1160 (1991). Briefly, specific mAbs, raised against inactivated and complexed α2-antiplasmin were coupled to sepharose beads and incubated with plasma samples. After washing the sepharose with phosphate buffered saline, bound complexes were subsequently incubated with $^{125}$I labeled mAbs to plasmin. After another washing procedure, sepharose-bound radioactivity was measured. As standards, serial dilution of plasma in which a maximal amount of PAP complexes was generated by incubation with two chain urokinase (Choay, Paris, France), after pre incubation of the plasma with methylamine to inactivate α2-macroglobulin were used. The results are expressed as nmol/L.

Statistical analysis of the results of these analyses are reflected in Tables 5 and 6. The mean±SEM results of assays of tissue plasminogen activator antigen, tissue plasminogen activator activity, tissue plasminogen activator inhibitor antigen, α2-plasmin inhibitor-plasmin complexes, urokinase type plasminogen activator and thrombin/antithrombin III complex are graphically represented in FIGS. 12, 13, 14, 15, 16 and 17, respectively.

TABLE 5

FIBRINOLYSIS

| Parameter | AUC hours | Median % change in AUC | p-value[a] | Statistical significance[b] |
|---|---|---|---|---|
| α2-antipl | 0–10 | −3% | .95 | NS |
| d-dimer | 0–10 | −45% | .31 | NS |
| plasminogen | 0–10 | −10% | .20 | NS |
| PAI Activity | 2–10 | −51% | .0304[c] | NS |
| PAP Complex | 0–10 | −51% | .0078 | S |
| uPA | 0–10 | −50% | .0078 | S |
| PAI Ag | 2–10 | −52% | .0078 | S |
| tPA Ag | 1–10 | −79% | .0078 | S |
| tPA Activity | 1–6 | −57% | .0078 | S |

[a]p-value comparing rBPI$_{23}$ vs. placebo AUC within each subject (Wilcoxon signed rank test).
[b]Statistical significance as determined by the Hochberg method (S = significant, NS = nonsignificant).
[c]Accounting for period effect.

TABLE 6

COAGULATION

| Parameter | AUC hours | Median % change in AUC | p-value[a] | Statistical significance[b] |
|---|---|---|---|---|
| Protein C Activity | 0–10 | −21% | .64 | NS |
| F1 + 2 | 1–10 | −31% | .0391 | NS |
| TAT Complex | 1–10 | −36% | .0078 | S |

[a]p-value comparing rBPI$_{23}$ vs. placebo AUC within each subject (Wilcoxon signed rank test).
[b]Statistical significance as determined by the Hochberg method (S = significant, NS = nonsignificant).

The placebo/endotoxin results in FIGS. 12 through 17 confirm a coordinated serological response to endotoxin administration in that shortly after tPA levels rise, there is sharp increase in tPA activity which precipitously drops upon increases in levels of circulating plasminogen activator inhibitor. The results demonstrate coordinated intervention in these related phenomena by treatment with a BPI-protein product. Peak levels in tPA are diminished and temporally shifted and a corresponding drop in tPA activity and circulating plasminogen activator inhibitor level is observed. Activation of plasminogen by tPA, as indicated by levels of circulating α2-plasmin inhibitor-plasmin complexes (PAP), was diminished. Thus, the present study reflects the first instance of intervention in endotoxin mediated increase in circulating tPA and its activity in experimental endotoxemia in humans.

EXAMPLE 6

Protection From Endotoxin-Induced Hyperdynamic Circulatory State

Circulatory state assessments were performed as follows: Echocardiograms were performed using an Ultramark 9 echocardiography machine (Advanced Technology Laboratories) with a 2.25 MHz phased array probe that featured a steerable pulsed Doppler mode. All subjects underwent basal echocardiography studies including M-mode measurements, 2-D imaging from parasternal, apical and subcostal views, color-coded Doppler imaging and pulsed Doppler measurements. Optimal parasternal and apical windows were obtained and marked on the subject's skin. All gain settings, sample volume size and depth and Doppler output settings were noted for each subject and carefully repeated at each measurement. The first basal study was performed several weeks before the first day of the infusion. On each infusion day a basal study was performed in the early morning one hour prior to the infusions. The fourth basal study was obtained six to eight weeks after the last infusion. Averages of these four echocardiograms comprise the basal values. On the study days at timepoint 1:30, 2:30, 4:00, 5:00, 8:00, 12:00 hours after start of infusion the following measurements were performed: M-mode; Left Ventricular End Diastolic Diameter (LVEDD), Left Ventricular End Systolic Diameter (LVESD). Interventricular Septal Thickness (IVS), Left Posterior Wall Thickness (LVPW), Dimension of the Aortic Root (Ao) and the Left Atrium (LA), tracings of the mitral valve motion and the aortic valve motion. 2-D: Standard parasternal longaxis and short-axis views, apical, and subcostal views were made to assess diameters, wall motion and aspect of reitrat, aortic and tricuspid valve apparatus. Careful measurement of the diameter of the left ventricular outflow tract (Dlvot) at its narrowest point approximately one centimeter below the aortic valve was performed in the parasternal long axis view on an early systolic still frame after aortic valve opening. At every time point at least six measurements were made. Color-Doppler: Mitral valve flow and tricuspid valve flow and regurgitation were assessed if present. Pulsed Doppler measurement: At the basal studies and on the study days at time points 0:30, 1:00, 1:30, 2:00, 2:30, 3:00, 3:30, 4:00, 4:30, 5:00, 6:00, 8:00, 10:00, 12:00 hours after the start of infusion a pulsed Doppler measurement of the systolic flow in the center of the left ventricular outflow tract from the apical 4-chamber view was obtained. Ten consecutive Doppler flow tracings were recorded on video-tape. Heart rate, temperature and blood pressure were simultaneously recorded. The Velocity Time Integral (VTI) or spectral area in meters is given by the sum of Vi·δt and was traced from the videotapes. Also the maximal velocity $V_{max}$ was noted from the VTI tracings. Averages were obtained of ten consecutive beats.

Equations employed to analyze results were as follows:

$$\text{Left Ventricular End Diastolic Volume: } LVEDV=(7.0/(2.4+LVEDD))*LVEDD^3, \quad (1)$$

$$\text{Left Ventricular End Systolic Volume: } LVESV=(7.0/(2.4+LVESD))*LVESD^3; \quad (2)$$

$$\text{Fractional Shortening: } SF=(LVEDD-LVESD)/LVEDD)*100; \quad (3)$$

$$\text{Ejection Fraction: } EF=(LVEDV-LVESV)/LVEDV)*100; \quad (4)$$

$$\text{Cross Sectional Area}_{lvot} \text{ in } cm^2: CSA=\pi(D_{lvot})^2/4; \quad (5)$$

$$\text{Stroke Volume in milliliters: } SV=CSA*VTI*100; \quad (6)$$

$$\text{Cardiac Output } (CO) \text{ in liters: } CO=SV*HR/1000 \quad (7)$$

where HR is Heart Rate (beats per minute);

$$\text{Cardiac Index } (L/min/m^2): CI=CO/BSA \quad (8)$$

where BSA is Body Surface Area; and

Systemic Vascular Resistance Index (dyne*$sec/cm^5$ per square meter): $SVRI=80*$(Mean Arterial Pressure−6)/Cardiac Index. (9)

Figure 18:
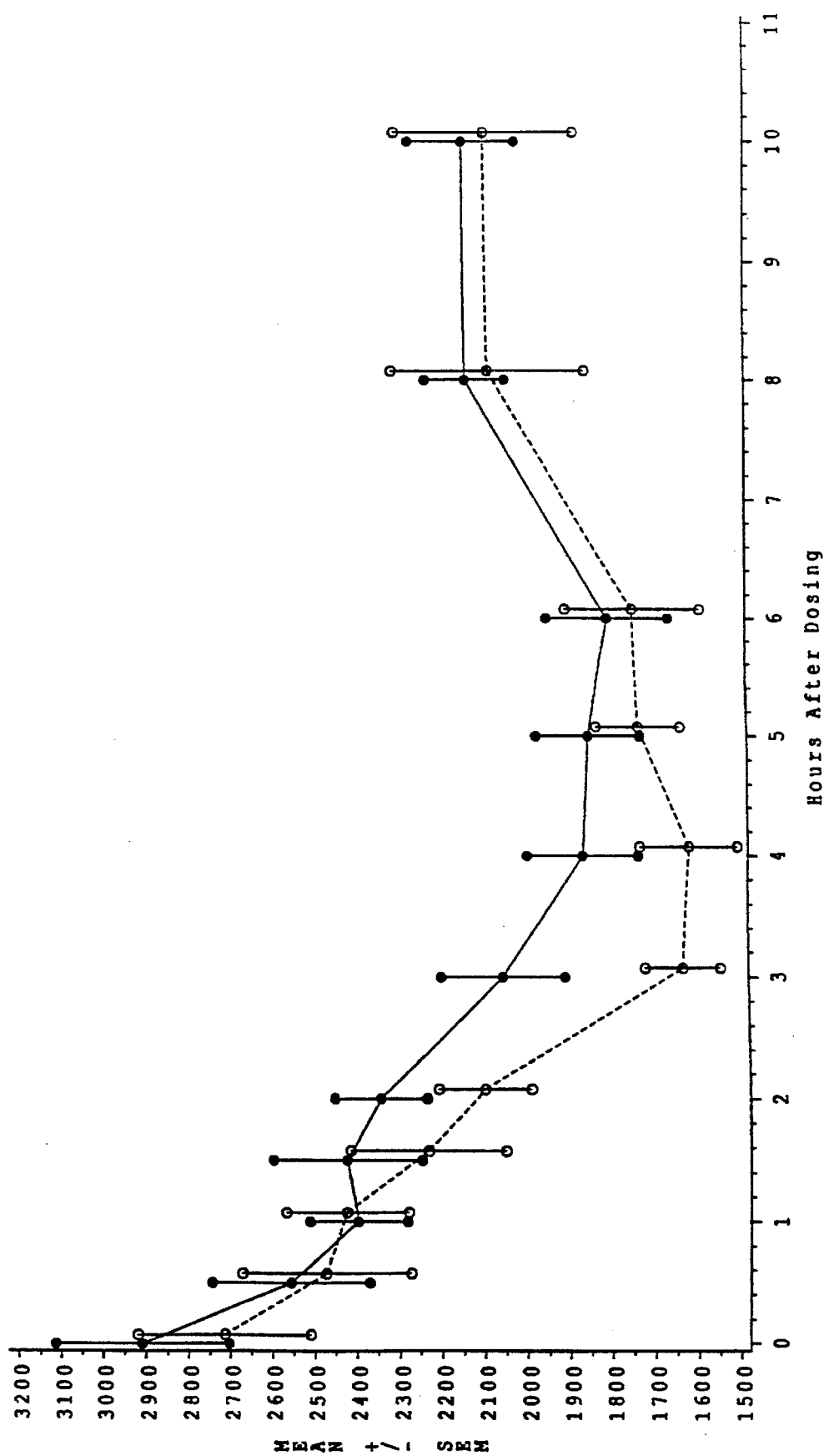
FIG. 18 is a graphic representation of the results of analysis of systematic vascular resistance index (SVRI)
Figure 19:
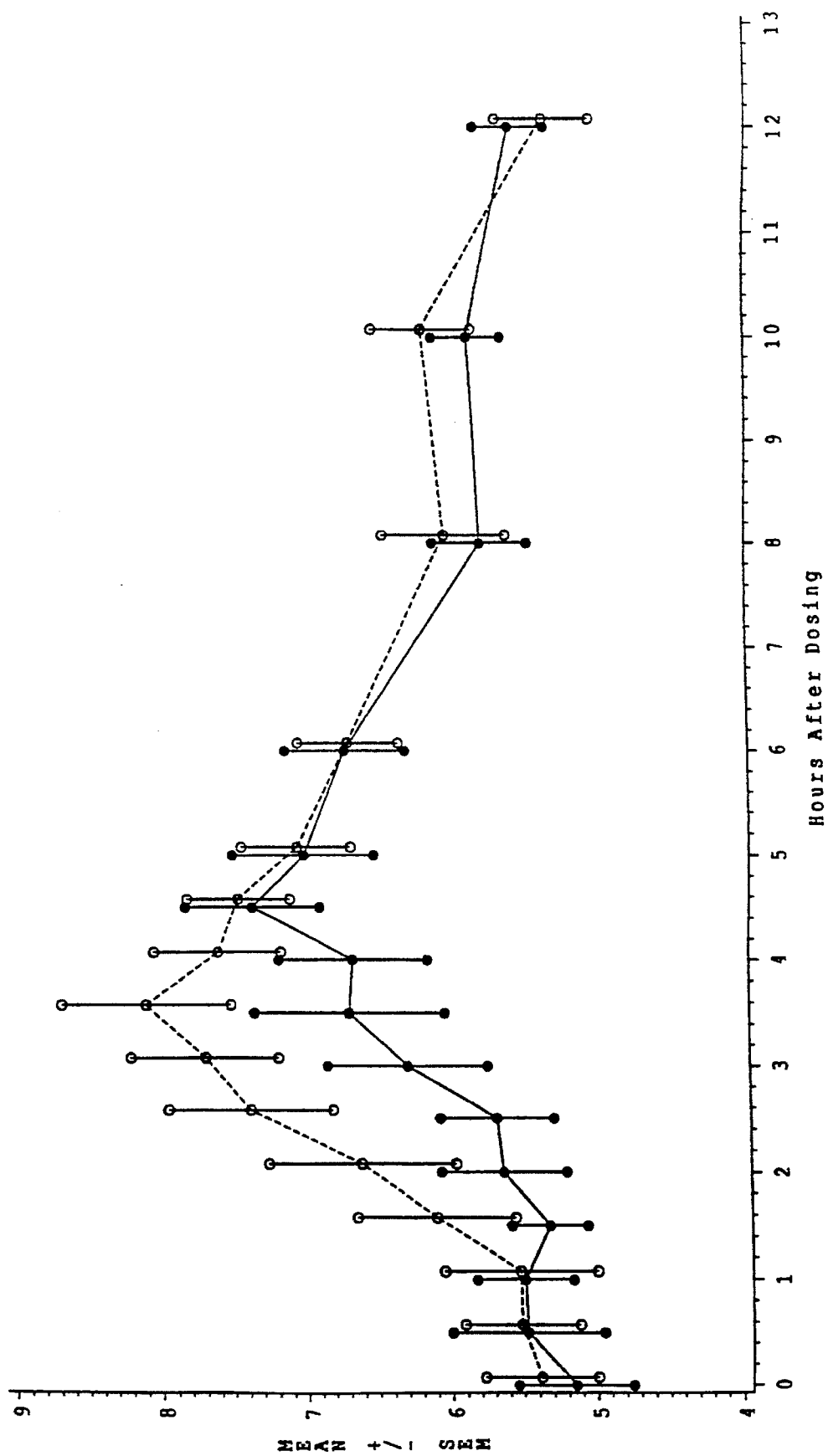
FIG. 19 is a graphic representation of the results of analysis of cardiac index (CI).

Table 7, below, sets out the results of statistical analysis of the primary left ventricular function parameters, SVRI and CI. Graphic representations of SVRI and CI data are provided in FIGS. 18 and 19 respectively.

TABLE 7

PRIMARY LEFT VENTRICULAR FUNCTION

| Parameter | Median % change in AUC[a] | p-value[b] | Statistical significance[c] |
|---|---|---|---|
| SVRI | +28% | .0304[d] | S |
| CI | −13% | .0156 | S |

[a]AUC calculated from hours 0–6.
[b]p-value comparing rBPI₂₃ vs. placebo within each subject (Wilcoxon signed rank test).
[c]Statistical significance as determined by the Hochberg method (S = significant, NS = nonsignificant) applied to primary analysis parameters.
[d]Accounting for period effect.

Table 8, below, sets forth data concerning percent change in median result values and p-values for the collateral assessments.

TABLE 8

COLLATERAL LEFT VENTRICULAR FUNCTION

| Parameter | Median % change in AUC[a] | p-value[b] |
|---|---|---|
| AO | −4% | .55 |
| CO | −11% | .0156 |
| EF | −10% | .64 |
| FS | −13% | .74 |
| HR | −27% | .0078 |
| IVS | +3% | .55 |
| LA | −15% | .38 |
| LVEDD | −4% | .95 |
| LVEDV | −4% | .84 |
| LVESD | +13% | .31[c] |
| LVESV | +14% | .31[c] |
| LVPW | +4% | .84 |

TABLE 8-continued

COLLATERAL LEFT VENTRICULAR FUNCTION

| Parameter | Median % change in AUC[a] | p-value[b] |
|---|---|---|
| SV | +9% | .15 |
| VTI | +1% | .55 |

[a]AUC calculated from hours 0–6.
[b]p-value comparing rBPI$_{23}$ vs. placebo within each subject (Wilcoxon signed rank test).
[c]Accounting for periof effect.

The above results establish that treatment of experimental endotoxemia in humans with a BPI protein product resulted in statistically significant modification of hyperdynamic changes in left ventricular function in response to endotoxin in circulation. The BPI protein product alleviated the decreases in systemic vascular resistance index and the concomitant increase in cardiac index which attend presence of endotoxin.

Numerous additional aspects and advantages of the present invention will be apparent to those skilled in the art upon consideration of the above illustrative examples of presently preferred practice thereof. For example, it will be apparent that human patients suffering from Gram negative bacteremia, accidental injection of endotoxin contaminated fluids or systemic release of endotoxin by translocation from the gut will benefit from administration of BPI protein products (by, e.g., continuous intravenous infusion) to provide serologically and hematologically verifiable reduction in endotoxin mediated increases in levels of circulating cytokines and tissue plasminogen activator and changes in numbers of neutrophils. It will also be apparent that BPI protein product administration will provide a beneficial adjunctive therapy for patients being treated with antibiotics and encountering entry of endotoxin into circulation as a result of bacterial lysis mediated by the antibiotic(s). Therefore only such limitations as appear in the appended claims should be placed upon the invention.

What is claimed is:

1. A method for treatment of sepsis or septic shock in humans exposed m bacterial endotoxin in circulation comprising administering a Bactericidal/Permeability-Increasing (BPI) protein product in an amount effective to alleviate endotoxin mediated increase in circulating tumor necrosis factor and interleukin 6.

2. A method for treatment of sepsis or septic shock in humans exposed to bacterial endotoxin in circulation comprising administering a BPI protein product in an amount effective to alleviate endotoxin mediated increase in circulating interleukin 8 and in neutrophil degranulation as characterized by increased circulating lactoferrin and/or elastase/α1 antitrypsin complexes.

3. A method for treatment of sepsis or septic shock in humans exposed to bacterial endotoxin in circulation comprising administering a BPI protein product in an mount effective to alleviate endotoxin mediated changes in numbers of circulating lymphocytes.

4. A method for treatment of sepsis or septic shock in humans exposed to bacterial endotoxin in circulation comprising administering a protein product in an mount effective to alleviate endotoxin mediated increase in circulating tissue plasminogen activator and tissue plasminogen activator activity.

5. A method for treatment of sepsis or septic shock in humans exposed to bacterial endotoxin in circulation comprising administering a BPI protein product in an amount effective to alleviate endotoxin-mediated decreases in systemic vascular resistance index.

6. The method of claim 1, 2, 3, 4 or 5 wherein the BPI protein product is administered in a dosage amount of from about 0.1 to 10.0 mg/kg of body weight.

7. In a human therapeutic method involving administration of a bacterial antibiotic, the improvement comprising administering a BPI protein product in an amount effective to alleviate endotoxin mediated increase in circulating tumor necrosis factor and interleukin 6.

8. In a human therapeutic method involving administration of a bacterial antibiotic, the improvement comprising administering a BPI protein product in an amount effective to alleviate endotoxin mediated increase in circulating interleukin 8 and in neutrophil degranulation as characterized by increased circulating lactoferrin and/or elastase/$\alpha$1 antitrypsin complexes.

9. In a human therapeutic method involving administration of a bacterial antibiotic, the improvement comprising administering a BPI protein product in an amount effective to alleviate endotoxin mediated changes in numbers of circulating lymphocytes.

10. In a human therapeutic method involving administration of a bacterial antibiotic, the improvement comprising administering a BPI protein product in an amount effective to alleviate endotoxin mediated increase in circulating tissue plasminogen activator and tissue plasminogen activator activity.

11. In a human therapeutic method involving administration of a bacterial antibiotic, the improvement comprising administering a BPI protein product in an amount effective to alleviate endotoxin mediated decreases in systemic vascular resistance index.

12. The improvement of claim 7, 8, 9, 10 or 11 wherein the BPI protein product is administered in a dosage amount of about 0.1 to about 10.0 mg/kg of body weight.

\* \* \* \* \*

UNITED STATES PATENT AND TRADEMARK OFFICE
CERTIFICATE OF CORRECTION

PATENT NO.   : 5,643,875
DATED        : July 1, 1997
INVENTOR(S)  : Friedmann et al.

It is certified that error appears in the above-identified patent and that said Letters Patent is hereby corrected as shown below:

Column 4,
Line 26, -- potentiation -- should replace "potentialion".
Line 67, -- Marra -- should replace "Matra".

Column 8,
Lines 4 and 40, -- alanine -- should replace "alaninc".
Line 5, -- GTT). -- should replace "GTF)."

Column 10,
Line 28, -- citrate -- should replace "titrate".

Column 13,
Line 42, -- $rBPI_{23}$ -- should replace "rBPI".
Line 60, -- Leukocyte -- should replace "Leukocyle".

Column 15,
Line 45, -- incubated -- should replace "inculcated".

Column 17,
Line 46, -- long-axis -- should replace "longaxis".
Line 48, -- mitral -- should replace "reitrat".

Column 25,
Line 57, -- to -- should replace "m".

Signed and Sealed this

Tenth Day of June, 2003

JAMES E. ROGAN
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC      54
                                 Met Arg Glu Asn Met Ala Arg Gly
                                 -31 -30                     -25

CCT TGC AAC GCG CCG AGA TGG GTG TCC CTG ATG GTG CTC GTC GCC ATA      102
Pro Cys Asn Ala Pro Arg Trp Val Ser Leu Met Val Leu Val Ala Ile
            -20                 -15                 -10

GGC ACC GCC GTG ACA GCG GCC GTC AAC CCT GGC GTC GTG GTC AGG ATC      150
Gly Thr Ala Val Thr Ala Ala Val Asn Pro Gly Val Val Val Arg Ile
        -5               1                    5

TCC CAG AAG GGC CTG GAC TAC GCC AGC CAG CAG GGG ACG GCC GCT CTG      198
Ser Gln Lys Gly Leu Asp Tyr Ala Ser Gln Gln Gly Thr Ala Ala Leu
10                  15              20                      25

CAG AAG GAG CTG AAG AGG ATC AAG ATT CCT GAC TAC TCA GAC AGC TTT      246
Gln Lys Glu Leu Lys Arg Ile Lys Ile Pro Asp Tyr Ser Asp Ser Phe
```

-continued

|  |  |  |  |  | 30 |  |  |  |  | 35 |  |  |  |  | 40 |  |  |
|---|---|---|---|---|---|---|---|---|---|---|---|---|---|---|---|---|---|
| AAG | ATC | AAG | CAT | CTT | GGG | AAG | GGG | CAT | TAT | AGC | TTC | TAC | AGC | ATG | GAC | | 294 |
| Lys | Ile | Lys | His | Leu | Gly | Lys | Gly | His | Tyr | Ser | Phe | Tyr | Ser | Met | Asp | | |
| | | | | 45 | | | | | 50 | | | | | 55 | | | |
| ATC | CGT | GAA | TTC | CAG | CTT | CCC | AGT | TCC | CAG | ATA | AGC | ATG | GTG | CCC | AAT | | 342 |
| Ile | Arg | Glu | Phe | Gln | Leu | Pro | Ser | Ser | Gln | Ile | Ser | Met | Val | Pro | Asn | | |
| | | | | 60 | | | | | 65 | | | | | 70 | | | |
| GTG | GGC | CTT | AAG | TTC | TCC | ATC | AGC | AAC | GCC | AAT | ATC | AAG | ATC | AGC | GGG | | 390 |
| Val | Gly | Leu | Lys | Phe | Ser | Ile | Ser | Asn | Ala | Asn | Ile | Lys | Ile | Ser | Gly | | |
| | | 75 | | | | | 80 | | | | | 85 | | | | | |
| AAA | TGG | AAG | GCA | CAA | AAG | AGA | TTC | TTA | AAA | ATG | AGC | GGC | AAT | TTT | GAC | | 438 |
| Lys | Trp | Lys | Ala | Gln | Lys | Arg | Phe | Leu | Lys | Met | Ser | Gly | Asn | Phe | Asp | | |
| 90 | | | | | 95 | | | | | 100 | | | | | 105 | | |
| CTG | AGC | ATA | GAA | GGC | ATG | TCC | ATT | TCG | GCT | GAT | CTG | AAG | CTG | GGC | AGT | | 486 |
| Leu | Ser | Ile | Glu | Gly | Met | Ser | Ile | Ser | Ala | Asp | Leu | Lys | Leu | Gly | Ser | | |
| | | | | 110 | | | | | 115 | | | | | 120 | | | |
| AAC | CCC | ACG | TCA | GGC | AAG | CCC | ACC | ATC | ACC | TGC | TCC | AGC | TGC | AGC | AGC | | 534 |
| Asn | Pro | Thr | Ser | Gly | Lys | Pro | Thr | Ile | Thr | Cys | Ser | Ser | Cys | Ser | Ser | | |
| | | | 125 | | | | | 130 | | | | | 135 | | | | |
| CAC | ATC | AAC | AGT | GTC | CAC | GTG | CAC | ATC | TCA | AAG | AGC | AAA | GTC | GGG | TGG | | 582 |
| His | Ile | Asn | Ser | Val | His | Val | His | Ile | Ser | Lys | Ser | Lys | Val | Gly | Trp | | |
| | | | 140 | | | | | 145 | | | | | 150 | | | | |
| CTG | ATC | CAA | CTC | TTC | CAC | AAA | AAA | ATT | GAG | TCT | GCG | CTT | CGA | AAC | AAG | | 630 |
| Leu | Ile | Gln | Leu | Phe | His | Lys | Lys | Ile | Glu | Ser | Ala | Leu | Arg | Asn | Lys | | |
| | 155 | | | | | 160 | | | | | 165 | | | | | | |
| ATG | AAC | AGC | CAG | GTC | TGC | GAG | AAA | GTG | ACC | AAT | TCT | GTA | TCC | TCC | AAG | | 678 |
| Met | Asn | Ser | Gln | Val | Cys | Glu | Lys | Val | Thr | Asn | Ser | Val | Ser | Ser | Lys | | |
| 170 | | | | | 175 | | | | | 180 | | | | | 185 | | |
| CTG | CAA | CCT | TAT | TTC | CAG | ACT | CTG | CCA | GTA | ATG | ACC | AAA | ATA | GAT | TCT | | 726 |
| Leu | Gln | Pro | Tyr | Phe | Gln | Thr | Leu | Pro | Val | Met | Thr | Lys | Ile | Asp | Ser | | |
| | | | | 190 | | | | | 195 | | | | | 200 | | | |
| GTG | GCT | GGA | ATC | AAC | TAT | GGT | CTG | GTG | GCA | CCT | CCA | GCA | ACC | ACG | GCT | | 774 |
| Val | Ala | Gly | Ile | Asn | Tyr | Gly | Leu | Val | Ala | Pro | Pro | Ala | Thr | Thr | Ala | | |
| | | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | | 822 |
| Glu | Thr | Leu | Asp | Val | Gln | Met | Lys | Gly | Glu | Phe | Tyr | Ser | Glu | Asn | His | | |
| | | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | | 870 |
| His | Asn | Pro | Pro | Pro | Phe | Ala | Pro | Pro | Val | Met | Glu | Phe | Pro | Ala | Ala | | |
| | 235 | | | | | 240 | | | | | 245 | | | | | | |
| CAT | GAC | CGC | ATG | GTA | TAC | CTG | GGC | CTC | TCA | GAC | TAC | TTC | TTC | AAC | ACA | | 918 |
| His | Asp | Arg | Met | Val | Tyr | Leu | Gly | Leu | Ser | Asp | Tyr | Phe | Phe | Asn | Thr | | |
| 250 | | | | | 255 | | | | | 260 | | | | | 265 | | |
| GCC | GGG | CTT | GTA | TAC | CAA | GAG | GCT | GGG | GTC | TTG | AAG | ATG | ACC | CTT | AGA | | 966 |
| Ala | Gly | Leu | Val | Tyr | Gln | Glu | Ala | Gly | Val | Leu | Lys | Met | Thr | Leu | Arg | | |
| | | | | 270 | | | | | 275 | | | | | 280 | | | |
| GAT | GAC | ATG | ATT | CCA | AAG | GAG | TCC | AAA | TTT | CGA | CTG | ACA | ACC | AAG | TTC | | 1014 |
| Asp | Asp | Met | Ile | Pro | Lys | Glu | Ser | Lys | Phe | Arg | Leu | Thr | Thr | Lys | Phe | | |
| | | | 285 | | | | | 290 | | | | | 295 | | | | |
| TTT | GGA | ACC | TTC | CTA | CCT | GAG | GTG | GCC | AAG | AAG | TTT | CCC | AAC | ATG | AAG | | 1062 |
| Phe | Gly | Thr | Phe | Leu | Pro | Glu | Val | Ala | Lys | Lys | Phe | Pro | Asn | Met | Lys | | |
| | | 300 | | | | | 305 | | | | | 310 | | | | | |
| ATA | CAG | ATC | CAT | GTC | TCA | GCC | TCC | ACC | CCG | CCA | CAC | CTG | TCT | GTG | CAG | | 1110 |
| Ile | Gln | Ile | His | Val | Ser | Ala | Ser | Thr | Pro | Pro | His | Leu | Ser | Val | Gln | | |
| | 315 | | | | | 320 | | | | | 325 | | | | | | |
| CCC | ACC | GGC | CTT | ACC | TTC | TAC | CCT | GCC | GTG | GAT | GTC | CAG | GCC | TTT | GCC | | 1158 |
| Pro | Thr | Gly | Leu | Thr | Phe | Tyr | Pro | Ala | Val | Asp | Val | Gln | Ala | Phe | Ala | | |
| 330 | | | | | 335 | | | | | 340 | | | | | 345 | | |
| GTC | CTC | CCC | AAC | TCC | TCC | CTG | GCT | TCC | CTC | TTC | CTG | ATT | GGC | ATG | CAC | | 1206 |
| Val | Leu | Pro | Asn | Ser | Ser | Leu | Ala | Ser | Leu | Phe | Leu | Ile | Gly | Met | His | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 350 |     |     |     |     | 355 |     |     |     |     | 360 |      |
| ACA | ACT | GGT | TCC | ATG | GAG | GTC | AGC | GCC | GAG | TCC | AAC | AGG | CTT | GTT | GGA | 1254 |
| Thr | Thr | Gly | Ser | Met | Glu | Val | Ser | Ala | Glu | Ser | Asn | Arg | Leu | Val | Gly |      |
|     |     |     | 365 |     |     |     |     | 370 |     |     |     |     | 375 |     |     |      |
| GAG | CTC | AAG | CTG | GAT | AGG | CTG | CTC | CTG | GAA | CTG | AAG | CAC | TCA | AAT | ATT | 1302 |
| Glu | Leu | Lys | Leu | Asp | Arg | Leu | Leu | Leu | Glu | Leu | Lys | His | Ser | Asn | Ile |      |
|     |     | 380 |     |     |     |     | 385 |     |     |     |     | 390 |     |     |     |      |
| GGC | CCC | TTC | CCG | GTT | GAA | TTG | CTG | CAG | GAT | ATC | ATG | AAC | TAC | ATT | GTA | 1350 |
| Gly | Pro | Phe | Pro | Val | Glu | Leu | Leu | Gln | Asp | Ile | Met | Asn | Tyr | Ile | Val |      |
|     | 395 |     |     |     |     | 400 |     |     |     |     | 405 |     |     |     |     |      |
| CCC | ATT | CTT | GTG | CTG | CCC | AGG | GTT | AAC | GAG | AAA | CTA | CAG | AAA | GGC | TTC | 1398 |
| Pro | Ile | Leu | Val | Leu | Pro | Arg | Val | Asn | Glu | Lys | Leu | Gln | Lys | Gly | Phe |      |
| 410 |     |     |     |     | 415 |     |     |     |     | 420 |     |     |     |     | 425 |      |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro | Ala | Arg | Val | Gln | Leu | Tyr | Asn | Val | Val | Leu | Gln |      |
|     |     |     | 430 |     |     |     |     | 435 |     |     |     |     | 440 |     |     |      |
| CCT | CAC | CAG | AAC | TTC | CTG | CTG | TTC | GGT | GCA | GAC | GTT | GTC | TAT | AAA |     | 1491 |
| Pro | His | Gln | Asn | Phe | Leu | Leu | Phe | Gly | Ala | Asp | Val | Val | Tyr | Lys |     |      |
|     |     |     | 445 |     |     |     |     | 450 |     |     |     |     | 455 |     |     |      |

| TGAAGGCACC | AGGGGTGCCG | GGGGCTGTCA | GCCGCACCTG | TTCCTGATGG | GCTGTGGGGC | 1551 |
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTTAGGGA | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTTCATG | TG         |            |            |            | 1813 |

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Arg | Glu | Asn | Met | Ala | Arg | Gly | Pro | Cys | Asn | Ala | Pro | Arg | Trp | Val |
|-----|-----|-----|-----|-----|-----|-----|-----|-----|-----|-----|-----|-----|-----|-----|-----|
| -31 |     | -30 |     |     | -25 |     |     |     |     | -20 |     |     |     |     |     |
| Ser | Leu | Met | Val | Leu | Val | Ala | Ile | Gly | Thr | Ala | Val | Thr | Ala | Ala | Val |
| -15 |     |     |     |     | -10 |     |     |     |     | -5  |     |     |     |     | 1   |
| Asn | Pro | Gly | Val | Val | Val | Arg | Ile | Ser | Gln | Lys | Gly | Leu | Asp | Tyr | Ala |
|     |     |     | 5   |     |     |     |     | 10  |     |     |     |     | 15  |     |     |
| Ser | Gln | Gln | Gly | Thr | Ala | Ala | Leu | Gln | Lys | Glu | Leu | Lys | Arg | Ile | Lys |
|     |     | 20  |     |     |     |     | 25  |     |     |     |     | 30  |     |     |     |
| Ile | Pro | Asp | Tyr | Ser | Asp | Ser | Phe | Lys | Ile | Lys | His | Leu | Gly | Lys | Gly |
|     | 35  |     |     |     |     | 40  |     |     |     |     | 45  |     |     |     |     |
| His | Tyr | Ser | Phe | Tyr | Ser | Met | Asp | Ile | Arg | Glu | Phe | Gln | Leu | Pro | Ser |
| 50  |     |     |     |     | 55  |     |     |     |     | 60  |     |     |     |     | 65  |
| Ser | Gln | Ile | Ser | Met | Val | Pro | Asn | Val | Gly | Leu | Lys | Phe | Ser | Ile | Ser |
|     |     |     |     | 70  |     |     |     |     | 75  |     |     |     |     | 80  |     |
| Asn | Ala | Asn | Ile | Lys | Ile | Ser | Gly | Lys | Trp | Lys | Ala | Gln | Lys | Arg | Phe |
|     |     |     | 85  |     |     |     |     | 90  |     |     |     |     | 95  |     |     |
| Leu | Lys | Met | Ser | Gly | Asn | Phe | Asp | Leu | Ser | Ile | Glu | Gly | Met | Ser | Ile |
|     |     | 100 |     |     |     |     | 105 |     |     |     |     | 110 |     |     |     |
| Ser | Ala | Asp | Leu | Lys | Leu | Gly | Ser | Asn | Pro | Thr | Ser | Gly | Lys | Pro | Thr |
|     | 115 |     |     |     |     | 120 |     |     |     |     | 125 |     |     |     |     |

```
Ile  Thr  Cys  Ser  Ser  Cys  Ser  Ser  His  Ile  Asn  Ser  Val  His  Val  His
130                      135                 140                           145

Ile  Ser  Lys  Ser  Lys  Val  Gly  Trp  Leu  Ile  Gln  Leu  Phe  His  Lys  Lys
                    150                      155                      160

Ile  Glu  Ser  Ala  Leu  Arg  Asn  Lys  Met  Asn  Ser  Gln  Val  Cys  Glu  Lys
               165                      170                      175

Val  Thr  Asn  Ser  Val  Ser  Ser  Lys  Leu  Gln  Pro  Tyr  Phe  Gln  Thr  Leu
          180                      185                      190

Pro  Val  Met  Thr  Lys  Ile  Asp  Ser  Val  Ala  Gly  Ile  Asn  Tyr  Gly  Leu
     195                 200                      205

Val  Ala  Pro  Pro  Ala  Thr  Thr  Ala  Glu  Thr  Leu  Asp  Val  Gln  Met  Lys
210                      215                 220                           225

Gly  Glu  Phe  Tyr  Ser  Glu  Asn  His  His  Asn  Pro  Pro  Pro  Phe  Ala  Pro
                    230                      235                           240

Pro  Val  Met  Glu  Phe  Pro  Ala  Ala  His  Asp  Arg  Met  Val  Tyr  Leu  Gly
               245                      250                      255

Leu  Ser  Asp  Tyr  Phe  Phe  Asn  Thr  Ala  Gly  Leu  Val  Tyr  Gln  Glu  Ala
          260                      265                      270

Gly  Val  Leu  Lys  Met  Thr  Leu  Arg  Asp  Asp  Met  Ile  Pro  Lys  Glu  Ser
     275                      280                 285

Lys  Phe  Arg  Leu  Thr  Thr  Lys  Phe  Phe  Gly  Thr  Phe  Leu  Pro  Glu  Val
290                      295                 300                           305

Ala  Lys  Lys  Phe  Pro  Asn  Met  Lys  Ile  Gln  Ile  His  Val  Ser  Ala  Ser
                    310                      315                      320

Thr  Pro  Pro  His  Leu  Ser  Val  Gln  Pro  Thr  Gly  Leu  Thr  Phe  Tyr  Pro
               325                      330                 335

Ala  Val  Asp  Val  Gln  Ala  Phe  Ala  Val  Leu  Pro  Asn  Ser  Ser  Leu  Ala
          340                      345                      350

Ser  Leu  Phe  Leu  Ile  Gly  Met  His  Thr  Thr  Gly  Ser  Met  Glu  Val  Ser
     355                      360                 365

Ala  Glu  Ser  Asn  Arg  Leu  Val  Gly  Glu  Leu  Lys  Leu  Asp  Arg  Leu  Leu
370                      375                 380                           385

Leu  Glu  Leu  Lys  His  Ser  Asn  Ile  Gly  Pro  Phe  Pro  Val  Glu  Leu  Leu
                    390                      395                      400

Gln  Asp  Ile  Met  Asn  Tyr  Ile  Val  Pro  Ile  Leu  Val  Leu  Pro  Arg  Val
               405                      410                      415

Asn  Glu  Lys  Leu  Gln  Lys  Gly  Phe  Pro  Leu  Pro  Thr  Pro  Ala  Arg  Val
          420                      425                      430

Gln  Leu  Tyr  Asn  Val  Val  Leu  Gln  Pro  His  Gln  Asn  Phe  Leu  Leu  Phe
     435                      440                      445

Gly  Ala  Asp  Val  Val  Tyr  Lys
450                      455
```